(12) United States Patent
Surman et al.

(10) Patent No.: US 10,684,268 B2
(45) Date of Patent: Jun. 16, 2020

(54) SENSOR SYSTEMS FOR MEASURING AN INTERFACE LEVEL IN A MULTI-PHASE FLUID COMPOSITION

(71) Applicant: BL Technologies, Inc., Minnetonka, MN (US)

(72) Inventors: Cheryl Margaret Surman, Albany, NY (US); Jon Albert Dieringer, Gurnee, IL (US); Radislav Alexandrovich Potyrailo, Niskayuna, NY (US)

(73) Assignee: BL Technologies, Inc., Minnetonka, MN (US)

( * ) Notice: Subject to any disclaimer, the term of this patent is extended or adjusted under 35 U.S.C. 154(b) by 588 days.

(21) Appl. No.: 14/697,086

(22) Filed: Apr. 27, 2015

(65) Prior Publication Data
US 2015/0233887 A1    Aug. 20, 2015

Related U.S. Application Data

(63) Continuation-in-part of application No. 13/630,587, filed on Sep. 28, 2012, now Pat. No. 9,658,178, and
(Continued)

(51) Int. Cl.
*G01N 27/02* (2006.01)
*G01N 33/28* (2006.01)

(52) U.S. Cl.
CPC ....... *G01N 33/2847* (2013.01); *G01N 27/023* (2013.01); *G01N 27/026* (2013.01); *G01N 33/2823* (2013.01)

(58) Field of Classification Search
CPC ............... G01N 27/023; G01N 27/026; G01N 33/2823; G01N 33/1833; G01N 33/2847
(Continued)

(56) References Cited

U.S. PATENT DOCUMENTS

D218,009 S    7/1970   Bosack
D219,617 S    12/1970  Swift
(Continued)

FOREIGN PATENT DOCUMENTS

CN    1363844 A    8/2002
CN    1532372 A    9/2004
(Continued)

OTHER PUBLICATIONS

Agar, G., P. Clewis, and C. Spencer, "Energy absorption probes control oily-water discharges", Hydrocarbon Processing, Aug. 1, 1993. 72(8): Abstract.
(Continued)

*Primary Examiner* — Peter J Macchiarolo
*Assistant Examiner* — Alexander A Mercado
(74) *Attorney, Agent, or Firm* — Meunier Carlin & Curfman LLC

(57) ABSTRACT

A sensor includes a resonant transducer, the resonant transducer being configured to determine the composition of an emulsion or other dispersion. The resonant transducer has a sampling cell, a bottom winding disposed around the sampling cell, and a top winding disposed around the bottom winding. The composition of the dispersion is determined by measuring the complex impedance spectrum values of the mixture of the dispersion and applying multivariate data analysis to the values.

20 Claims, 19 Drawing Sheets

Related U.S. Application Data a continuation-in-part of application No. 13/630,739, filed on Sep. 28, 2012, now Pat. No. 9,176,083.

(60) Provisional application No. 61/987,853, filed on May 2, 2014.

(58) Field of Classification Search
USPC .................................. 73/61.43, 64.44, 61.61
See application file for complete search history.

(56) References Cited

U.S. PATENT DOCUMENTS

| | | | |
|---|---|---|---|
| 3,675,121 A | 7/1972 | Thompson | |
| 3,778,706 A | 12/1973 | Thompson | |
| 3,927,369 A | 12/1975 | Billeter et al. | |
| 4,096,385 A | 6/1978 | Marett | |
| 4,273,636 A | 6/1981 | Shimada et al. | |
| 4,275,364 A | 6/1981 | Skatvold, Jr. | |
| 4,372,164 A | 2/1983 | Brown et al. | |
| 4,553,434 A | 11/1985 | Spaargaren | |
| 4,728,892 A | 3/1988 | Vinegar et al. | |
| 4,820,989 A | 4/1989 | Vail, III | |
| 4,844,097 A | 7/1989 | Bellhouse et al. | |
| 4,876,512 A | 10/1989 | Kroeger et al. | |
| 4,882,542 A | 11/1989 | Vail, III | |
| 4,887,455 A | 12/1989 | Payne et al. | |
| 4,887,798 A * | 12/1989 | Julius ..................... G01F 23/26 266/227 | |
| 4,922,745 A | 5/1990 | Rudkin et al. | |
| 4,941,958 A | 7/1990 | Byers | |
| 4,965,522 A | 10/1990 | Hazen et al. | |
| 4,996,490 A | 2/1991 | Scott et al. | |
| 5,010,301 A | 4/1991 | Leung et al. | |
| 5,025,346 A | 6/1991 | Tang et al. | |
| 5,059,790 A | 10/1991 | Klainer et al. | |
| 5,089,780 A | 2/1992 | Megerle | |
| 5,157,338 A | 10/1992 | Motherbaugh et al. | |
| 5,208,165 A | 5/1993 | Law et al. | |
| 5,241,364 A | 8/1993 | Kimura | |
| 5,260,569 A | 11/1993 | Kimura | |
| 5,306,644 A | 4/1994 | Myerholtz et al. | |
| 5,344,547 A | 9/1994 | Vlasov et al. | |
| 5,421,983 A | 6/1995 | Slack et al. | |
| 5,443,985 A | 8/1995 | Lu et al. | |
| 5,497,140 A | 3/1996 | Tuttle | |
| 5,543,722 A * | 8/1996 | Suzuki ................ G01N 33/2852 324/663 | |
| 5,585,729 A | 12/1996 | Toshima et al. | |
| 5,591,896 A | 1/1997 | Lin | |
| 5,592,040 A | 1/1997 | Yamamoto | |
| 5,607,566 A | 3/1997 | Brown et al. | |
| 5,646,592 A | 7/1997 | Tuttle | |
| 5,672,319 A | 9/1997 | Eisum | |
| 5,744,902 A | 4/1998 | Vig | |
| 5,751,475 A | 5/1998 | Ishiwata et al. | |
| 5,754,055 A | 5/1998 | McAdoo et al. | |
| 5,785,181 A | 7/1998 | Quartararo, Jr. | |
| 5,786,595 A | 7/1998 | Herron et al. | |
| 5,817,943 A | 10/1998 | Welles, II et al. | |
| 5,831,439 A | 11/1998 | Suenram et al. | |
| 5,840,168 A | 11/1998 | Chaniotakis et al. | |
| 5,874,047 A | 2/1999 | Schoning et al. | |
| 5,961,923 A | 10/1999 | Nova et al. | |
| 6,025,725 A | 2/2000 | Gershenfeld et al. | |
| 6,025,783 A | 2/2000 | Steffens, Jr. | |
| 6,111,520 A | 8/2000 | Allen et al. | |
| 6,166,546 A | 12/2000 | Scheihing et al. | |
| 6,189,656 B1 | 2/2001 | Morgenstern et al. | |
| 6,192,753 B1 | 2/2001 | Czarnek | |
| 6,204,764 B1 | 3/2001 | Maloney | |
| 6,278,379 B1 | 8/2001 | Allen et al. | |
| 6,287,765 B1 | 9/2001 | Cubicciotti | |
| 6,359,444 B1 | 3/2002 | Grimes | |
| 6,360,585 B1 | 3/2002 | Potyrailo et al. | |
| 6,398,931 B1 | 6/2002 | Burchette et al. | |
| 6,399,375 B2 | 6/2002 | Vajta | |
| 6,406,668 B1 | 6/2002 | Dordick et al. | |
| 6,461,872 B1 | 10/2002 | Sivavec et al. | |
| 6,471,838 B1 | 10/2002 | Igel et al. | |
| 6,506,346 B1 | 1/2003 | Monro | |
| 6,544,193 B2 | 4/2003 | Abreu | |
| 6,586,946 B2 | 7/2003 | Hefti et al. | |
| 6,614,229 B1 | 9/2003 | Clark et al. | |
| 6,657,429 B1 | 12/2003 | Goldfine et al. | |
| 6,672,512 B2 | 1/2004 | Bridgelall | |
| 6,676,903 B2 | 1/2004 | Potyrailo et al. | |
| 6,730,201 B1 | 5/2004 | Kuhlman et al. | |
| 6,751,557 B1 | 6/2004 | Shehab et al. | |
| 6,771,074 B2 | 8/2004 | Zou et al. | |
| 6,773,926 B1 | 8/2004 | Freund et al. | |
| 6,780,307 B2 | 8/2004 | Kidwell | |
| 6,782,736 B1 * | 8/2004 | Hammer ................. G01F 23/26 73/304 C | |
| 6,804,544 B2 | 10/2004 | Van Antwerp et al. | |
| 6,818,450 B2 | 11/2004 | Eaton et al. | |
| 6,864,801 B2 | 3/2005 | Tabanou et al. | |
| 6,891,383 B2 | 5/2005 | Nicholson et al. | |
| 6,911,818 B2 * | 6/2005 | Julius ................. B22D 11/186 324/204 | |
| 6,953,520 B2 | 10/2005 | Yengoyan et al. | |
| 7,017,404 B1 | 3/2006 | Kain | |
| 7,031,560 B2 | 4/2006 | Lelong-Feneyrou et al. | |
| 7,034,660 B2 | 4/2006 | Watters et al. | |
| 7,038,470 B1 | 5/2006 | Johnson | |
| 7,076,858 B2 | 7/2006 | Eckstein et al. | |
| 7,113,125 B2 | 9/2006 | Le Sesne | |
| 7,126,013 B2 | 10/2006 | Heeney et al. | |
| 7,168,310 B2 | 1/2007 | Al-Ruwaili | |
| 7,171,312 B2 | 1/2007 | Steinthal et al. | |
| 7,178,416 B2 | 2/2007 | Whelan et al. | |
| 7,204,128 B1 | 4/2007 | Liu et al. | |
| 7,252,010 B2 | 8/2007 | Ohta et al. | |
| 7,276,916 B2 | 10/2007 | Hammer | |
| 7,293,450 B2 | 11/2007 | Liu et al. | |
| 7,317,989 B2 | 1/2008 | Difoggio et al. | |
| 7,335,336 B1 | 2/2008 | Kim | |
| 7,343,800 B2 | 3/2008 | Harman et al. | |
| 7,350,367 B2 | 4/2008 | Matsiev et al. | |
| 7,434,457 B2 | 10/2008 | Goodwin et al. | |
| 7,445,143 B2 | 11/2008 | Pang et al. | |
| 7,449,893 B1 | 11/2008 | Tsironis | |
| 7,455,108 B2 | 11/2008 | Jenkins et al. | |
| 7,456,744 B2 | 11/2008 | Kuhns | |
| 7,466,041 B2 | 12/2008 | Urman | |
| 7,481,771 B2 | 1/2009 | Fonseca et al. | |
| 7,483,743 B2 | 1/2009 | Mann et al. | |
| 7,486,495 B1 | 2/2009 | Diederichs et al. | |
| 7,495,454 B2 | 2/2009 | Rivera | |
| 7,523,647 B2 | 4/2009 | Scott | |
| 7,562,557 B2 | 7/2009 | Bennett et al. | |
| 7,569,810 B1 | 8/2009 | Troxler et al. | |
| 7,629,167 B2 | 12/2009 | Hodge et al. | |
| 7,677,307 B2 | 3/2010 | Vasques et al. | |
| 7,808,235 B2 | 10/2010 | Rollins et al. | |
| 7,812,609 B2 | 10/2010 | Martinez et al. | |
| 7,814,786 B2 | 10/2010 | Woodard | |
| 7,911,345 B2 | 3/2011 | Potyrailo et al. | |
| 7,948,380 B2 | 5/2011 | Kuhns et al. | |
| 7,948,385 B2 | 5/2011 | Potyrailo et al. | |
| 7,958,772 B2 | 6/2011 | Permuy et al. | |
| 7,969,307 B2 | 6/2011 | Peeters | |
| 8,018,342 B2 | 9/2011 | Monk et al. | |
| 8,111,143 B2 | 2/2012 | Tong et al. | |
| 8,155,891 B2 | 4/2012 | Kong et al. | |
| 8,159,347 B2 | 4/2012 | Potyrailo et al. | |
| 8,184,290 B2 | 5/2012 | Hertens et al. | |
| 8,190,394 B2 | 5/2012 | Davis et al. | |
| 8,215,166 B2 | 7/2012 | Cunningham et al. | |
| 8,232,091 B2 | 7/2012 | Maltezos et al. | |
| 8,246,910 B2 | 8/2012 | Dhirani et al. | |
| 8,261,618 B2 | 9/2012 | Engle et al. | |
| 8,318,099 B2 | 11/2012 | Potyrailo et al. | |
| 8,342,242 B2 | 1/2013 | Roddy et al. | |
| 8,429,985 B2 | 4/2013 | Furlong | |

(56) References Cited

U.S. PATENT DOCUMENTS

| | | |
|---|---|---|
| 8,452,716 B2 | 5/2013 | Howley et al. |
| 8,468,871 B2 | 6/2013 | Potyrailo et al. |
| 8,508,368 B2 | 8/2013 | Potyrailo et al. |
| 8,542,024 B2 | 9/2013 | Potyrailo et al. |
| 8,547,110 B2 | 10/2013 | Kesil et al. |
| 8,643,388 B2 | 2/2014 | Hedges |
| 8,676,436 B2 | 3/2014 | Raimarckers et al. |
| 8,710,973 B2 | 4/2014 | Schneider et al. |
| 8,732,938 B2 | 5/2014 | Kolosov et al. |
| 8,736,425 B2 | 5/2014 | Potyrailo |
| 8,833,145 B2 | 9/2014 | Fischer et al. |
| 8,933,706 B1 | 1/2015 | Karlquist |
| 8,952,708 B2 | 2/2015 | Nikolenko |
| 9,074,966 B2 | 7/2015 | Sanderlin et al. |
| 9,536,122 B2 | 1/2017 | Potyrailo |
| 2001/0045355 A1 | 11/2001 | Gephart et al. |
| 2002/0050929 A1 | 5/2002 | Parrotta et al. |
| 2002/0081231 A1 | 6/2002 | Shapiro et al. |
| 2002/0089356 A1 | 7/2002 | Perrott et al. |
| 2002/0149466 A1 | 10/2002 | Sunshine et al. |
| 2002/0173040 A1 | 11/2002 | Potyrailo et al. |
| 2002/0177232 A1 | 11/2002 | Melker et al. |
| 2003/0053936 A1 | 3/2003 | Potyrailo et al. |
| 2003/0154031 A1 | 8/2003 | Potyrailo et al. |
| 2003/0169032 A1 | 9/2003 | Minchole et al. |
| 2003/0179024 A1 | 9/2003 | Montagnana |
| 2003/0232223 A1 | 12/2003 | Leddy et al. |
| 2004/0015990 A1 | 1/2004 | Suematsu et al. |
| 2004/0035211 A1 | 2/2004 | Pinto et al. |
| 2004/0051154 A1 | 3/2004 | Yamakawa et al. |
| 2004/0113790 A1 | 6/2004 | Hamel et al. |
| 2004/0125442 A1 | 7/2004 | Yun et al. |
| 2004/0155667 A1 | 8/2004 | Kesil et al. |
| 2004/0189487 A1 | 9/2004 | Hoefel et al. |
| 2004/0219523 A1 | 11/2004 | Stanton et al. |
| 2004/0227682 A1 | 11/2004 | Anderson |
| 2004/0248315 A1 | 12/2004 | Klein et al. |
| 2005/0022581 A1 | 2/2005 | Sunshine |
| 2005/0058460 A1 | 3/2005 | Wang |
| 2005/0093760 A1 | 5/2005 | Rochelle et al. |
| 2005/0161405 A1* | 7/2005 | Holland ............... C02F 1/485 |
| | | 210/695 |
| 2005/0193832 A1 | 9/2005 | Tombs et al. |
| 2005/0199731 A9 | 9/2005 | Empedocles et al. |
| 2005/0261562 A1 | 11/2005 | Zhou et al. |
| 2006/0014172 A1 | 1/2006 | Muller et al. |
| 2006/0020427 A1 | 1/2006 | Kahn et al. |
| 2006/0055531 A1 | 3/2006 | Cook et al. |
| 2006/0081471 A1 | 4/2006 | Kidwell |
| 2006/0133720 A1 | 6/2006 | Hochberg et al. |
| 2006/0141469 A1 | 6/2006 | Rossier et al. |
| 2006/0198760 A1 | 9/2006 | Potyrailo et al. |
| 2006/0205093 A1 | 9/2006 | Prins |
| 2006/0210440 A1 | 9/2006 | Potyrailo et al. |
| 2006/0238349 A1 | 10/2006 | Hu et al. |
| 2006/0265150 A1 | 11/2006 | Hu et al. |
| 2007/0029195 A1 | 2/2007 | Li et al. |
| 2007/0064839 A1 | 3/2007 | Luu |
| 2007/0084277 A1 | 4/2007 | Steinsiek |
| 2007/0085686 A1 | 4/2007 | Oz |
| 2007/0090926 A1 | 4/2007 | Potyrailo et al. |
| 2007/0111222 A1 | 5/2007 | Chasin et al. |
| 2007/0131418 A1 | 6/2007 | Barrow et al. |
| 2007/0148670 A1 | 6/2007 | O'Malley |
| 2007/0176773 A1 | 8/2007 | Smolander et al. |
| 2007/0236338 A1 | 10/2007 | Maruyama |
| 2007/0241890 A1 | 10/2007 | Yoshioka |
| 2008/0090926 A1 | 4/2008 | Kang et al. |
| 2008/0093219 A1 | 4/2008 | Goldberg et al. |
| 2008/0116908 A1 | 5/2008 | Potyrailo et al. |
| 2008/0135614 A1 | 6/2008 | Werner et al. |
| 2008/0142366 A1 | 6/2008 | Tamirisa et al. |
| 2008/0157901 A1 | 7/2008 | Matekovits et al. |
| 2008/0177150 A1 | 7/2008 | Il et al. |
| 2008/0179197 A1 | 7/2008 | Wu |
| 2008/0180249 A1 | 7/2008 | Butler et al. |
| 2008/0184787 A1 | 8/2008 | Coates |
| 2008/0191859 A1 | 8/2008 | Tiek et al. |
| 2008/0236814 A1 | 10/2008 | Roddy |
| 2008/0280374 A1 | 11/2008 | Potyrailo et al. |
| 2009/0035856 A1 | 2/2009 | Galliher et al. |
| 2009/0039864 A1 | 2/2009 | Gordon |
| 2009/0087862 A1 | 4/2009 | Carter et al. |
| 2009/0095073 A1 | 4/2009 | Fukumura et al. |
| 2009/0104707 A1 | 4/2009 | Wang et al. |
| 2009/0120169 A1 | 5/2009 | Chandler et al. |
| 2009/0189741 A1 | 7/2009 | Rowland et al. |
| 2009/0204250 A1 | 8/2009 | Potyrailo et al. |
| 2009/0215646 A1 | 8/2009 | Anslyn et al. |
| 2009/0256679 A1 | 10/2009 | Potyrailo et al. |
| 2009/0265037 A1 | 10/2009 | Bassa |
| 2009/0278685 A1* | 11/2009 | Potyrailo ............. G06K 7/0095 |
| | | 340/572.1 |
| 2009/0289776 A1 | 11/2009 | Moore et al. |
| 2009/0308155 A1 | 12/2009 | Zhang |
| 2010/0021993 A1 | 1/2010 | Wang et al. |
| 2010/0042338 A1 | 2/2010 | Giurgiutiu et al. |
| 2010/0059221 A1 | 3/2010 | Vannuffelen et al. |
| 2010/0075405 A1 | 3/2010 | Broadley et al. |
| 2010/0102004 A1* | 4/2010 | Holland .................. C02F 1/48 |
| | | 210/695 |
| 2010/0109766 A1 | 5/2010 | Nilsson et al. |
| 2010/0134286 A1 | 6/2010 | Potyrailo et al. |
| 2010/0138267 A1 | 6/2010 | Vittal et al. |
| 2010/0153323 A1 | 6/2010 | Hennessy et al. |
| 2010/0231407 A1 | 9/2010 | Carr |
| 2010/0250170 A1 | 9/2010 | Kalinin et al. |
| 2010/0261226 A1 | 10/2010 | Niazi |
| 2010/0280788 A1 | 11/2010 | Bohan et al. |
| 2010/0295558 A1* | 11/2010 | Eberheim ............ G01N 27/023 |
| | | 324/654 |
| 2011/0006878 A1 | 1/2011 | Nyffeler et al. |
| 2011/0006900 A1 | 1/2011 | Nyffeler et al. |
| 2011/0012736 A1 | 1/2011 | Potyrailo et al. |
| 2011/0018649 A1 | 1/2011 | David et al. |
| 2011/0022318 A1 | 1/2011 | Zhao et al. |
| 2011/0029156 A1 | 2/2011 | Vernacchia et al. |
| 2011/0045601 A1 | 2/2011 | Gryska et al. |
| 2011/0051775 A1 | 3/2011 | Ivanov et al. |
| 2011/0117538 A1 | 5/2011 | Niazi |
| 2011/0152706 A1 | 6/2011 | Christopherson et al. |
| 2011/0152750 A1 | 6/2011 | Dacey, Jr. et al. |
| 2011/0156177 A1 | 6/2011 | Merz |
| 2011/0160681 A1 | 6/2011 | Dacey, Jr. et al. |
| 2011/0166812 A1 | 7/2011 | Potyrailo et al. |
| 2011/0221667 A1 | 9/2011 | Lee |
| 2011/0248825 A1 | 10/2011 | Hamel et al. |
| 2011/0263036 A1 | 10/2011 | Blauw et al. |
| 2011/0282540 A1 | 11/2011 | Armitage et al. |
| 2011/0283821 A1 | 11/2011 | Ober et al. |
| 2011/0320142 A1 | 12/2011 | Surman et al. |
| 2012/0001730 A1 | 1/2012 | Potyrailo et al. |
| 2012/0004851 A1 | 1/2012 | Potyrailo et al. |
| 2012/0025526 A1 | 2/2012 | Luo et al. |
| 2012/0053881 A1 | 3/2012 | Schulz et al. |
| 2012/0166095 A1 | 6/2012 | Potyrailo et al. |
| 2012/0231504 A1 | 9/2012 | Niazi |
| 2012/0235690 A1 | 9/2012 | Potyrailo et al. |
| 2012/0258441 A1 | 10/2012 | Gebauer et al. |
| 2012/0265036 A1 | 10/2012 | Estes et al. |
| 2012/0289757 A1 | 11/2012 | Boyden et al. |
| 2013/0041334 A1 | 2/2013 | Prioleau et al. |
| 2013/0060112 A1 | 3/2013 | Pryor et al. |
| 2013/0154847 A1 | 6/2013 | Potyrailo et al. |
| 2013/0182819 A1 | 7/2013 | Dvorkin et al. |
| 2013/0285677 A1* | 10/2013 | Hammer ............ G01R 27/2611 |
| | | 324/655 |
| 2014/0002111 A1 | 1/2014 | Potyrailo et al. |
| 2014/0028330 A1 | 1/2014 | Potyrailo et al. |
| 2014/0090451 A1 | 4/2014 | Surman et al. |
| 2014/0090454 A1 | 4/2014 | Surman et al. |
| 2014/0091811 A1 | 4/2014 | Potyrailo et al. |
| 2014/0095102 A1 | 4/2014 | Potyrailo et al. |
| 2014/0182362 A1 | 7/2014 | Potyrailo et al. |

(56) References Cited

U.S. PATENT DOCUMENTS

| | | | |
|---|---|---|---|
| 2014/0182363 A1 | 7/2014 | Potyrailo et al. | |
| 2014/0305194 A1* | 10/2014 | Surman | G01F 23/26 73/61.44 |
| 2015/0185173 A1 | 7/2015 | Potyrailo et al. | |
| 2015/0233887 A1 | 8/2015 | Surman et al. | |
| 2016/0187277 A1 | 6/2016 | Potyrailo et al. | |

FOREIGN PATENT DOCUMENTS

| | | | |
|---|---|---|---|
| CN | 2809215 | Y | 8/2006 |
| CN | 1865966 | A | 11/2006 |
| CN | 101022760 | A | 8/2007 |
| CN | 101057124 | A | 10/2007 |
| CN | 201000455 | Y | 1/2008 |
| CN | 101988574 | A | 3/2011 |
| CN | 102022264 | A | 4/2011 |
| CN | 102422330 | A | 4/2012 |
| CN | 203923208 | U | 11/2014 |
| EP | 0159270 | A2 | 10/1985 |
| EP | 1173613 | A2 | 1/2002 |
| EP | 2498076 | A1 | 9/2012 |
| GB | 793953 | | 4/1958 |
| GB | 793953 | A | 4/1958 |
| JP | 5774097 | A | 5/1982 |
| JP | 59116855 | U | 8/1984 |
| JP | 59160746 | A | 9/1984 |
| JP | 0381659 | A | 4/1991 |
| JP | 06160317 | A | 6/1994 |
| JP | 06194333 | A | 7/1994 |
| JP | 6086057 | U | 12/1994 |
| JP | 0773282 | A | 3/1995 |
| JP | 07120423 | A | 5/1995 |
| JP | 08509549 | A | 10/1996 |
| JP | 09292453 | A | 11/1997 |
| JP | 10504388 | A | 4/1998 |
| JP | 2000111547 | A | 4/2000 |
| JP | 2001502791 | A | 2/2001 |
| JP | 2002125206 | A | 4/2002 |
| JP | 2003503011 | A | 1/2003 |
| JP | 2003506706 | A | 2/2003 |
| JP | 2003161637 | A | 6/2003 |
| JP | 2005156569 | A | 6/2005 |
| JP | 2006516721 | A | 7/2006 |
| JP | 2007516509 | A | 6/2007 |
| JP | 2008129009 | A | 6/2008 |
| JP | 2008236617 | A | 10/2008 |
| JP | 2008298565 | A | 12/2008 |
| JP | 2009092633 | A | 4/2009 |
| JP | 2009538433 | A | 11/2009 |
| JP | 2009540292 | A | 11/2009 |
| JP | 2011258627 | A | 12/2011 |
| RU | 2085921 | C1 | 7/1997 |
| WO | 9845779 | A1 | 10/1998 |
| WO | 0055583 | A1 | 9/2000 |
| WO | 200107874 | | 2/2001 |
| WO | 0173380 | A1 | 10/2001 |
| WO | 0212129 | A1 | 2/2002 |
| WO | 0223176 | A1 | 3/2002 |
| WO | 03034051 | A1 | 4/2003 |
| WO | 2003/050529 | | 6/2003 |
| WO | 03050529 | A1 | 6/2003 |
| WO | 2004/025288 | | 3/2004 |
| WO | 2004032191 | A2 | 4/2004 |
| WO | 2007075619 | A1 | 7/2007 |
| WO | 2007101992 | A1 | 9/2007 |
| WO | 2007109772 | A2 | 9/2007 |
| WO | 2008082654 | A2 | 7/2008 |
| WO | 2009/092633 | | 4/2009 |
| WO | 2012/050460 | | 4/2012 |
| WO | 2013057630 | A1 | 4/2013 |
| WO | 2014/051985 | | 4/2014 |
| WO | 2014/051989 | | 4/2014 |
| WO | 2015090358 | A1 | 6/2015 |
| WO | 2015128050 | A1 | 9/2015 |

OTHER PUBLICATIONS

Alary, V. and J. Falcimaigne, "Subsea water separation: a cost-effective solution for ultra deep water production". 17th World Petroleum Congress, Sep. 1-5, 2002, Rio de Janeiro, Brazil, 2002.
Asskildt, K. and P. Hansson, "New measuring sensor for level detection in subsea separators", ABB Review, Apr. 1999(4): p. 11-17.
Bennett, M.A. and R.A. Williams, "Monitoring the operation of an oil/water separator using impedance tomography" Minerals Engineering, 2004. 17(5): p. 605-614.
Casanella, R., 0. Casas, and R. Pallas-Areny, "Continuous liquid level measurement using a linear electrode array" Measurement Science and Technology, May 9, 2007. 18(7): p. 1859-1866.
Casanella et al. "Oil-Water Interface Level Sensor Based on an Electrode Array", Instrumentation and Measurement Technology Conference, 2006. IMTC 2006. Proceedings of the IEEE, pp. 710-713, Sorrento, Italy, Apr. 24-27, 2006.
Christian Michelsen Research, A.S., Ultrasonic Interface Level Detector. 2008, PO Box 6031, N05892 Bergen, Norway, www.crm.no.
Chuang, J., D.J. Thomson, and G.E. Bridges, "Embeddable wireless strain sensor based on resonant rf cavities", Rev. Sci. Instrum. 2005. 76: p. 1-7, published online Sep. 20, 2005.
Fauveau, E. and K. Hambrice, "Guided-wave radar helps level-detection in harsh settings Control Engineering" Mar. 2003. 50(3), 16.
Fransen, G. "New control system detects desalter problems before upsets occur". Apr. 2004, Agar Corporation, Prepared for presentation at The Aiche 2004 Spring National Meeting.
Garcia-Golding, F., et al., "Sensor for determining the water content of oil-in-water emulsion by specific admittance measurement", Sensors and Actuators: A. Physical, 1995, 47(1-3), 337-341.
Grimes, C.A., et al., "Wireless Magnetoelastic Resonance Sensors: A Critical Review. Sensors", Jul. 2002. 2, 294-313.
Gutzeit, J., "Controlling Crude Unit Overhead Corrosion—Rules of Thumb for Better Crude Desalting". NACE—International Corrosion Conference Series 2007, 075671-0756721.
Hewitt, "Oil/Water Interface Control for Desalters", Petroleum Technology Quarterly 2007, vol. No. 12, Issue No. 5, pp. 75-78, 2007.
Holstad, M.B., et al., "Scattered Gamma Radiation Utilized for Level Measurements in Gravitational Separators". IEEE Sensors Journal, Apr. 2005, 5(2), 175-182.
Hutzler, S., et al., "Measurement of Foam Density Profiles Using AC capacitance". Europhysics Letters, Sep. 10, 1995. 31 (8), 497-502.
Hwili, A. and W. Yang, "Multi-modality multi-interface level measurement", Journal of Physics: Conference Series, 2007, 76(1), 1-6.
Hwili, A. and W. Yang. "A single rod multi-modality multi-interface level sensor using an AC current source", IEEE International Workshop on Imaging Systems and Techniques, Sep. 10-12, 2008.
International Search Report and Written Opinion, dated Dec. 12, 2013, received in connection with International Application No. PCT/US2013/058932.
International Preliminary Report on Patentability and Written Opinion, dated Mar. 31, 2015, received in connection with International Application No. PCT/US2013/058932.
International Search Report and Written Opinion, dated Dec. 18, 2013, received in connection with International Application No. PCT/US2013/058898.
International Preliminary Report on Patentability and Written Opinion, dated Mar. 31, 2015, received in connection with International Application No. PCT/US2013/058898.
Isaksen, 0., A.S. Dico, and E.A. Hammer, "A capacitance-based tomography system for interface measurement in separation vessels", Measurement Science and Technology, Jun. 1994, 5(10): p. 1262-1271.
Jaworski, A.J. and G. Meng, "On-line measurement of separation dynamics in primary gas/oil/water separators: Challenges and technical solutions—A review". Journal of Petroleum Science and Engineering, 2009. 68, 47-59.

(56) References Cited

OTHER PUBLICATIONS

Jaworski, A.J. and T. Dyakowski, "Measurements of oil-water separation dynamics in primary separation systems using distributed capacitance sensors", Flow Measurement and Instrumentation, 2005. 16(2-3): p. 113-127.
Jaworski, A.J., T. Dyakowski, and G.A. Davies, "A capacitance probe for interface detection in oil and gas extraction plant", Measurement Science and Technology, Jan. 1999, 10(3), L 15-L20.
Lee, R.P., "Increase oil production and reduce chemical usage through separator level measurement by density profiling" ISA TECH/EXPO Technology Update Conference Proceedings 2001. 416: p. 321-328.
Meng, G., A.J. Jaworski, and J.C.S. Kimber, "A multi-electrode capacitance probe for phase detection in oil-water separation processes: Design, modelling and validation", Measurement Science and Technology, Mar. 2006. 17(4): p. 881-894.
Notice of Allowance, dated Jun. 18, 2015, received in connection with U.S. Appl. No. 13/630,739.
Pal, R., "Techniques for measuring the composition (oil and water content) of emulsions—a state of the art review. Colloids and Surfaces A: Physicochemical and Engineering Aspects", 1994. 84: 141-193.
Pasquale, M., "Mechanical sensors and actuators". Sensors and Actuators, A: Physical, 2003, 106(1-3), 142-148.
Potyrailo, R.A., et al., "Integration of passive multivariable RFID sensors into single-use biopharmaceutical manufacturing components", RFID 2010: International IEEE Conference on RFID, Jan. 7, 2010.
Sakharov, V.E., et al., "Liquid level sensor using ultrasonic Lamb waves". Ultrasonics, 2003, 41, 319-322.
Schuller, R.B., M. Halleraker, and B. Engebretsen, "Advanced Profile Gauge for Multiphase Systems. 1st World Congress on Industrial Process Tomography", Buxton, Greater Manchester, Apr. 14-17, 1999.
Shi, T.M., et al., "Capacitance-based instrumentation for multi-interface level measurement", Measurement Science and Technology, May 17, 1991, 2, 923-933.
Yang, W.Q., M.R. Brant, and M.S. Beck, "A multi-interface level measurement system using a segmented capacitance sensor for for separators", Measurement Science and Technology, Jul. 19, 1994. 5, 1177-1180.
Yang, W., "Sensors and instrumentation for monitoring and control of multi-phase separation". Measurement and Control, Jul. 2006. 39(6), 178-184.
Sen et al., "The Frequency Dependent Dielectric and Conductivity Response of Sedimentary Rocks", Journal of Microwave Power, vol. No. 18, Issue No. 1, pp. 95-105, Mar. 1983.
Wensink, "Dielectric Properties of Wet Soils in the Frequency Range 1-3000 MHz", Geophysical Prospecting, vol. No. 41, Issue No. 6, pp. 671-696, Jul. 1993.
Ishida et al., "Effects of pH on Dielectric Relaxation of Montmorillonite, Allophane, and Imogolite Suspensions", Journal of Colloid and Interface Science, vol. No. 212, Issue No. 1, pp. 152-161, May 1999.
Kaya, "Electrical Spectroscopy of Kaolin and Bentonite Slurries", Turkish Journal of Engineering and Environmental Sciences, vol. No. 25, Issue No. 4, pp. 345-354, Jan. 2001.
Seyfried et al., "Measurement of Soil Water Content with a 50-MHz Soil Dielectric Sensor", Soil Science Society of America Journal, vol. No. 68, Issue No. 2, pp. 394-403, Mar. 2004.
Ikenishi et al., "The Dielectric Characteristics of Agricultural Land for On-site and Real Time Measurement", SICE Annual Conference, Sapporo, vol. No. 2, pp. 1489-1492, Aug. 4-6, 2004.
Jimenez et al., "Surface Characterization of Clay Particles via Dielectric Spectroscopy", Annales Universitatis Mariae Curie-Sklodowska, vol. No. 63, Issue No. 7, pp. 73-86, Jan. 2008.
Sobrov et al., "The Effect of Clay and Organic Matter Content on the Dielectric Permittivity of Soils and Grounds at the Frequency Range from 10 MHz to 1 GHz", International Geoscience and Remote Sensing Symposium, Honolulu pp. 4433-4435, Jul. 25-30, 2010.
Owenier et al., "Dielectric Permittivity of Geologic Materials at Different Water Contents—Measurements with an Impedance Analyzer", 6th International Workshop on Advanced Ground Penetrating Radar, Aachen, pp. 1-5, Jun. 22-24, 2011.
Vasilyeva et al., "Differences in Behaviour of Adsorbed Water in Kaolinites and Montmorillonites in Temperature Range from −90° C. to +140° C. by Dielectric Spectroscopy", Journal of Physics Conference Series, vol. No. 394, Issue No. 1, pp. 1-6, Nov. 2012.
Swiech et al., "Dielectric Properties of Synthetic Oil Sands", Society of Petroleum Engineers—SPE Heavy Oil Conference, Calgary, Alberta, Canada, pp. 1-11, Jun. 11-13, 2013.
PCT Search Report and Written Opinion issued in connection with related PCT Application No. PCT/US2015/027482 dated Jul. 15, 2015.
Unofficial English Translation of Chinese Office Action issued in connection with related CN Application No. 201380050788.0 dated Jan. 20, 2016.
Cheung et al., "Impedance Spectroscopy Flow Cytometry: On-Chip Label-Free Cell Differentiation", Cytometry Part A, vol. No. 65, Issue No. 2, pp. 124-132, Jun. 2005.
Jang et al., "Chemical Sensors Based on Highly Conductive Poly(3,4-Ethylene-Dioxythiophene) Nanorods", Advanced Materials, vol. No. 17, Issue No. 13, pp. 1616-1620, Jul. 1, 2005.
Rakow et al., "Molecular Recognition and Discrimination of Amines with a Colorimetric Array", Angewandte Chemie, vol. No. 44, Issue No. 29, pp. 4528-4532, Jul. 18, 2005.
Zhang et al., "A Calorimetric Sensor Array for Organics in Water", Journal of the American Chemical Society, vol. No. 127, Issue No. 33, pp. 11548-11549, Aug. 2, 2005.
Chuang et al., "Embeddable Wireless Strain Sensor Based on Resonant RF Cavities", Review of Scientific Instruments, vol. No. 76, Issue No. 9, pp. 094703-094703-7, Sep. 2005.
Burnell et al., "Synthesis and Electrooptical Properties of Copolymers Derived from Phenol-Functionalized Telechelic Oligofluorenes", Macromolecules, vol. No. 38, Issue No. 26, pp. 10667-10677, Nov. 19, 2005.
Bang et al., "A Novel Electrochemical Detection Method for Aptamer Biosensors", Biosensors and Bioelectronics, vol. No. 21, Issue No. 6, pp. 863-870, Dec. 15, 2005.
Lange et al., "Measuring Biomolecular Binding Events with a Compact Disc Player Device", Angewandte Chemie International Edition, vol. No. 45, Issue No. 2, pp. 270-273, Dec. 23, 2005.
Locklin et al., "Effect of Morphology on Organic Thin Film Transistor Sensors", Analytical and Bioanalytical Chemistry, vol. No. 384, Issue No. 2, pp. 336-342, 2006.
Morris et al., "Wireless Sensor Array System for Combinatorial Screening of Sensor Materials", Materials Research Society Symposium Proceedings, vol. No. 894, pp. 0894-LL07-02.1-0894-LL07-02.6, 2006.
Lvovich et al., "Impedance Characterization of Industrial Lubricants", Electrochimica Acta, vol. No. 51, Issue No. 8-9, pp. 1487-1496, Jan. 20, 2006.
Yang et al., "Chemical Identification Using an Impedance Sensor Based on Dispersive Charge Transport", Applied Physics Letters, vol. No. 88, Issue No. 7, pp. 074104-1-074104-3, Feb. 2006.
Meng et al., "A Multi-Electrode Capacitance Probe for Phase Detection in Oil-Water Separation Processes: Design, Modelling and Validation", Measurement Science and Technology, vol. No. 17, Issue No. 4, pp. 881-894, Mar. 23, 2006.
Casanella et al., "Oil-water Interface Level Sensor Based on an Electrode Array", Proceedings of the IEEE Instrumentation and Measurement Technology Conference, Sorrento, Italy, pp. 710-713, Apr. 24-27, 2006.
Yang, "Sensors and Instrumentation for Monitoring and Control of Multi-Phase Separation", Measurement and Control, vol. No. 39, Issue No. 6, pp. 1-12, Jul. 1, 2006.
Pejcic et al., "Impedance Spectroscopy: Over 35 Years of Electrochemical Sensor Optimization", Electrochimica Acta, vol. No. 51, Issue No. 28, pp. 6217-6229, Sep. 15, 2006.

(56) References Cited

OTHER PUBLICATIONS

Benini et al., "Wireless Sensor Networks: Enabling Technology for Ambient Intelligence", Microelectronics Journal, vol. No. 37, Issue No. 12, pp. 1639-1649, Dec. 2006.
Potyrailo et al., "Multianalyte Chemical Identification and Quantitation Using a Single Radio Frequency Identification Sensor", Analytical Chemistry, vol. No. 79, Issue No. 1, pp. 45-51, 2007.
Li et al., "Chemosensory Performance of Molecularly Imprinted Fluorescent Conjugated Polymer Materials", Journal of the American Chemical Society, vol. No. 129, Issue No. 51, pp. 15911-15918, 2007.
Wang et al., "Array of Molecularly Mediated Thin Film Assemblies of Nanoparticles: Correlation of Vapor Sensing with Interparticle Spatial Properties", Journal of the American Chemical Society, vol. No. 129, Issue No. 7, pp. 2161-2170, 2007.
Hewitt, "Oil/Water Interface Control for Desalters", Petroleum Technology Quarterly, vol. No. 12, Issue No. 5, pp. 75-78, 2007.
Hwili et al., "Multi-Modality Multi-Interface Level Measurement", Journal of Physics: Conference Series, vol. No. 76, Issue No. 1, pp. 1-6, 2007.
Hempel et al., "Application of a Portable RF Impedance Spectrum Analyzer for the Investigation of Lateral Field Excited Acoustic Wave Sensors in a Liquid Environment", Ultrasonics Symposium Proceeding, vol. No. 1, pp. 373-376, Jan. 1, 2007.
Hwang et al., "Photoelectron Spectroscopic Study of the Electronic Band Structure of Polyfluorene and Fluorene-Arylamine Copolymers at Interfaces", The Journal of Physical Chemistry C, vol. No. 111, Issue No. 3, pp. 1378-1384, Jan. 2007.
Qing et al., "RFID Tag Antennas", Antennas for Portable Devices, John Wiley & Sons, Ltd, pp. 59-61; 65-69, Mar. 2007.
Bai et al., "Gas Sensors Based on Conducting Polymers", Sensors, vol. No. 7, Issue No. 3, pp. 267-307, Mar. 2007.
Gutzeit, "Controlling Crude Unit Overhead Corrosion—Rules of Thumb for Better Crude Desalting", NACE International Corrosion Conference & Expo, Nashville, Tennessee, pp. 1-21, Mar. 11-15, 2007 abstract.
Casanella et al., "Continuous Liquid Level Measurement Using a Linear Electrode Array", Measurement Science and Technology, vol. No. 18, Issue No. 7, pp. 1859-1866, May 9, 2007.
Metzger et al., "Weight-Sensitive Foam to Monitor Product Availability on Retail Shelves", 5th International Conference on Pervasive Computing, Toronto, Canada, vol. No. 4480, pp. 268-279, May 13-16, 2007.
Li et al., "Inkjet Printed Chemical Sensor Array Based on Polythiophene Conductive Polymers", Sensors and Actuators B: Chemical, vol. No. 123, Issue No. 2, pp. 651-660, May 21, 2007.
Liu et al., "Measurement of Density and Viscosity of Dodecane and Decane with a Piezoelectric Tuning Fork Over 298-448 K and 0.1-137.9 MPa", Sensors and Actuators A Physical, vol. No. 167, Issue No. 2, pp. 347-353, Jun. 2007.
Lu et al., "MEMS-Based Inductively Coupled RFID Transponder for Implantable Wireless Sensor Applications", IEEE Transactions on Magnetics, vol. No. 43, Issue No. 6, pp. 2412-2414, Jun. 2007.
Wei et al., "Simple and Sensitive Aptamer-Based Colorimetric Sensing of Protein using Unmodified Gold Nanoparticle Probes", Chemical Communications, Issue 36, pp. 3735-3737, Jun. 29, 2007.
Potyrailo et al., "Wireless Resonant Sensor Array for High-Throughput Screening of Materials", Review of Scientific Instruments, vol. No. 78, Issue No. 7, pp. 072214-1-072214-6, Jul. 2007.
Sugiyasu et al., "Conducting-Polymer-Based Chemical Sensors: Transduction Mechanisms", Bulletin of the Chemical Society of Japan, vol. No. 80, Issue No. 11, pp. 2074-2083, Aug. 2007.
Armani et al., "Label-Free Single-Molecule Detection with Optical Microcavities", Science, vol. No. 317, Issue No. 5839, pp. 783-787, Aug. 10, 2007.
Tan et al., "A Wireless, Passive Sensor for Quantifying Packaged Food Quality", Sensors, vol. No. 7, Issue No. 9, pp. 1747-1756, Sep. 2007.
Wang et al., "A New Method for On-line Monitoring of Brake Fluid Condition using an Enclosed Reference Probe", Measurement Science and Technology, vol. No. 18, Issue No. 11, pp. 3625-3635, Oct. 16, 2007.
Wang et al., "A Gold Nanoparticle-Based Aptamer Target Binding Readout for ATP Assay", Advanced Materials, vol. No. 19, Issue No. 22, pp. 3943-3946, Nov. 2007.
Tanaka et al., "Quartz Crystal Capacitive Sensor with Inductance-Capacitance Resonance Circuit for Vapor Sensing", Japanese Journal of Applied Physics, vol. No. 46, Issue No. 11, pp. 7509-7511, Nov. 2007.
Ulrich et al., "Simultaneous Estimation of Soot and Diesel Contamination in Engine Oil Using Electrochemical Impedance Spectroscopy", Sensors and Actuators B: Chemical, vol. No. 127, Issue No. 2, pp. 613-618, Nov. 15, 2007.
Husebo, "Ultrasonic Interface Level Detector", Christian Michelsen Research AS, pp. 1-2, 2008.
Surman et al., "Quantitation of Toxic Vapors in Variable Humidity Atmosphere Using Individual Passive Radio Frequency Identification (RFID) Sensors", 12th International Meeting on Chemical Sensors, Columbus, pp. 1-2, 2008.
Potyrailo et al., "Modeling of Selectivity of Multi-Analyte Response of Passive Radio Frequency Identification (RFID) Sensors", 12th International Meeting on Chemical Sensors, Columbus, pp. 1-3, 2008.
Wang et al., "Sensors and Biosensors for the Determination of Small Molecule Biological Toxins", Sensors, vol. No. 8, Issue No. 9, pp. 6045-6054, 2008.
Hendrick, "Cellulose Acetate Fibers with Fluorescing Nanoparticles for Anti-Counterfeiting Purposes", Erin Sue Hendrick, pp. 1-36, 2008.
Jimenez et al., "Surface Characterization of Clay Particles via Dielectric Spectroscopy", Annales Universitatis Mariae Curie-Sklodowska, vol. No. 63, Issue No. 1, pp. 73-86, Jan. 2008.
Metzger et al., "Flexible-Foam-Based Capacitive Sensor Arrays for Object Detection at Low Cost", Applied Physics Letters, vol. No. 92, Issue No. 1, pp. 013506-1-013506-3, Jan. 2008.
Hatchett et al., "Composites of Intrinsically Conducting Polymers as Sensing Nanomaterials", Chemical Reviews, vol. No. 108, Issue No. 2, pp. 746-769, Jan. 3, 2008.
Joo et al., "Chemical Sensors with Integrated Electronics", Chemical Reviews, vol. No. 108, Issue No. 2, pp. 638-651, Jan. 10, 2008.
Rock et al., "Electronic Nose: Current Status and Future Trends", Chemical Reviews, vol. No. 108, Issue No. 2, pp. 705-725, Jan. 19, 2008.
Diamond et al., "Wireless Sensor Networks and Chemo-/Biosensing", Chemical Reviews, vol. No. 108, Issue No. 2 , pp. 652-679, Jan. 24, 2008.
Wang et al., "Aptamer Biosensor for Protein Detection Using Gold Nanoparticles", Analytical Biochemistry, vol. No. 373, Issue No. 2, pp. 213-219, Feb. 15, 2008.
Agoston et al., "A Concept of an Infrared Sensor System for Oil Condition Monitoring", Elektrotechnik & Informationstechnik, vol. No. 125, Issue No. 3, pp. 71-75, Mar. 2008.
Wang et al., "Electrochemical Sensors for Clinic Analysis", Sensors, vol. No. 8, Issue No. 4, pp. 2043-2081, Apr. 2008.
Capone et al., "Metal Oxide Gas Sensor Array for the Detection of Diesel Fuel in Engine Oil", Sensors and Actuators B: Chemical, vol. No. 131, Issue No. 1, pp. 125-133, Apr. 14, 2008.
Potyrailo et al., "Position-Independent Chemical Quantitation with Passive 13.56-MHz Radio Frequency Identification (RFID) Sensors", Talanta, vol. No. 75, Issue No. 3, pp. 624-628, May 15, 2008.
Hempel et al., "Lateral Field Excited Quartz Crystal Resonator Sensors for Determination of Acoustic and Electrical Properties of Liquids", IEEE International Frequency Control Symposium, Honolulu, Hawaii, pp. 705-710, May 19-21, 2008.
Palacios et al., "Rational Design of a Minimal Size Sensor Array for Metal Ion Detection", Journal of the American Chemical Society, vol. No. 130, Issue No. 31, pp. 10307-10314, Jul. 11, 2008.
Kauffman et al., "Carbon Nanotube Gas and Vapor Sensors", Angewandte Chemie International Edition, vol. No. 47, pp. 6550-6570, Jul. 18, 2008.

(56) References Cited

OTHER PUBLICATIONS

Zheng et al., "Resonance Impedance Sensing of Human Blood Cells", Sensors and Actuators A: Physical, vol. No. 145-146, pp. 29-36, Jul.-Aug. 2008.
Guan et al., "Engine Lubricating Oil Classification by SAE Grade and Source Based on Dielectric Spectroscopy Data", Analytica Chimica Acta, vol. No. 628, Issue No. 1, pp. 117-120, Oct. 17, 2008.
Li et al., "Chemical Sensing Using Nanostructured Polythiophene Transistors", Nano Letters, vol. No. 8, Issue No. 11, pp. 3563-3567, Oct. 28, 2008.
Hwili et al., "A Single Rod Multi-Modality Multi-Interface Level Sensor using an AC Current Source", IEEE International Workshop on Imaging Systems and Techniques, Chania, Greece, pp. 1-5, Sep. 10-12, 2008.
Wudy et al., "Rapid Impedance Scanning QCM for Electrochemical Applications Based on Miniaturized Hardware and High-Performance Curve Fitting", Electrochimica Acta, vol. No. 53, Issue No. 22, pp. 6568-6574, Sep. 20, 2008.
Potyrailo et al., "RFID Sensors Based on Ubiquitous Passive 13.56-MHz RFID Tags and Complex Impedance Detection", Wireless Communications and Mobile Computing, pp. 1-13, Nov. 2008.
Saltas et al., "Dielectric Properties of Non-Swelling Bentonite: The Effect of Temperature and Water Saturation", Journal of Non-Crystalline Solids, vol. No. 354, Issue No. 52-54, pp. 5533-5541, Dec. 15, 2008.
Sacristan-Riquelme et al., "Low Power Impedance Measurement Integrated Circuit for Sensor Applications", Microelectronics Journal, vol. No. 40, Issue No. 1, pp. 177-184, Jan. 2009.
Ertl et al., "Interdigitated Impedance Sensors for Analysis of Biological Cells in Microfluidic Biochips", Elektrotechnik & Informationstechnik, vol. No. 126, Issue No. 1, pp. 47-50, Jan.-Feb. 2009.
Potyrailo et al., "Passive Radio Frequency Identification (RFID) Chemical Sensors for Homeland Security Applications", Wiley Handbook of Science and Technology for Homeland Security, pp. 1-12, Jun. 15, 2009.
Potyrailo et al., "Selective Detection of Chemical Species in Liquids and Gases Using Passive Radio-Frequency Identification (RFID) Sensors", IEEE Conference on Transducers, Denver, CO, USA, pp. 1650-1653, Jun. 21-25, 2009.
Potyrailo et al., "Combinatorial Screening of Polymeric Sensing Materials Using RFID Sensors", Journal of Combinatorial Chemistry, vol. No. 11, Issue No. 4, pp. 598-603, Jul.-Aug. 2009.
Jaworski et al., "On-line Measurement of Separation Dynamics in Primary Gas/Oil/Water Separators: Challenges and Technical Solutions—A review", Journal of Petroleum Science and Engineering, vol. No. 68, Issue No. 1-2, pp. 47-59, Sep. 2009.
McCann et al., "Recent Advances in Lateral Field Excited and Monolithic Spiral Coil Acoustic Transduction Bulk Acoustic Wave Sensor Platforms", Measurement Science and Technology, vol. No. 20, Issue No. 12, pp. 124001-1-124001-12, Oct. 2009.
Westafer et al., "Functionalization of High Frequency SAW RFID Devices for Ozone Dosimetry", IEEE Sensors Conference, pp. 1747-1752, Oct. 25-28, 2009.
Niedermayer et al., "Yet Another Precision Impedance Analyzer (YAPIA)—Readout Electronics for Resonating Sensors", Sensors and Actuators A: Physical, vol. No. 156, Issue No. 1, pp. 245-250, Nov. 2009.
Potyrailo et al., "Development of Radio-Frequency Identification Sensors Based on Organic Electronic Sensing Materials for Selective Detection of Toxic Vapors", Journal of Applied Physics, vol. No. 106, Issue No. 12, pp. 124902-1-124902-6, Dec. 2009.
Mortier et al., "Chemistry and Technology of Lubricants", Third Edition, Springer, pp. 1-560, 2010.
Cho et al., "Capacitive Sensor for Automotive Engine Oil Degradation using Wireless Network", International Symposium on Advanced Packaging Materials: Microtech, Cambridge, pp. 88-91, Mar. 2, 2010.
Potyrailo et al., "Selective Quantitation of Vapors and their Mixtures using Individual Passive Multivariable RFID Sensors", IEEE International Conference on RFID, Orlando, Florida, pp. 22-28, Apr. 14-16, 2010.
Potyrailo et al., "Integration of Passive Multivariable RFID Sensors into Single-Use Biopharmaceutical Manufacturing Components", IEEE International Conference on RFID, Orlando, Florida, pp. 1-7, Apr. 14-16, 2010.
Becher et al., "The Detection of Evaporating Hazardous Material Released from Moving Sources Using a Gas Sensor Network", Sensors and Actuators B: Chemical, vol. No. 146, Issue No. 2, pp. 513-520, Apr. 29, 2010.
Alexander et al., "Optimization of Interdigitated Electrode (IDE) Arrays for Impedance Based Evaluation of Hs 578T Cancer Cells", Journal of Physics: Conference Series, vol. No. 224, Issue No. 1, pp. 012134-1-012134-4, May 2010.
Bobrov et al., "The Effect of Clay and Organic Matter Content on the Dielectric Permittivity of Soils and Grounds at the Frequency Range from 10 MHz to 1 GHz", International Geoscience and Remote Sensing Symposium (IGARSS), pp. 4433-4435, Jul. 25-30, 2010.
Chen et al., "Based on ZigBee Wireless Sensor Network the Monitoring System Design for Production Process Toxic and Harmful Gas", International Conference on Computer, Mechatronics, Control and Electronic Engineering, vol. No. 4, pp. 425-428, Aug. 24-26, 2010.
Hong et al., "Development of a Micro Liquid-Level Sensor for Harsh Environments using a Periodic Heating Technique", Measurement Science and Technology, vol. No. 21, Issue No. 10, Sep. 2010.
Bianchi et al., "Model of an Interdigitated Microsensor to Detect and Quantify Cells Flowing in a Test Chamber", 6th Annual COMSOL Conference, Paris, pp. 1-5, Nov. 2010.
Wang et al., "Flexible Chemiresistor Sensors: Thin film Assemblies of Nanoparticles on a Polyethylene Terephthalate Substrate", Journal of Materials Chemistry, vol. No. 20, pp. 907-915, Dec. 15, 2010.
Suresh et al., "Piezoelectric Based Resonant Mass Sensor using Phase Measurement", Measurement, vol. No. 44, Issue No. 2, pp. 320-325, Feb. 2011.
De Vito et al., "Wireless Sensor Networks for Distributed Chemical Sensing: Addressing Power Consumption Limits with On-Board Intelligence", IEEE Sensors Journal, vol. No. 11, Issue No. 14, pp. 947-955, Apr. 2011.
Potyrailo et al., "Passive Multivariable Temperature and Conductivity RFID Sensors for Single-Use Biopharmaceutical Manufacturing Components", Biotechnology Progress, vol. No. 27, Issue No. 3, pp. 875-884, May 2, 2011.
Sen et al., "Evaluation of Sensor Arrays for Engine Oils Using Artificial Oil Alteration", Proceedings of SPIE 8066, Smart Sensors Actuators and MEMS, vol. No. 8066, pp. 1-7, May 5, 2011.
Owenier et al., "Dielectric Permittivity of Geologic Materials at Different Water Contents—Measurements with an Impedance Analyzer", 6th International Workshop on Advanced Ground Penetrating Radar (IWAGPR), Aachen, Germany, pp. 1-5, Jun. 22-24, 2011.
Guan et al.,"Application of Dielectric Spectroscopy for Engine Lubricating Oil Degradation Monitoring", Sensors and Actuators A: Physical, vol. No. 168, Issue No. 1, pp. 22-29, Jul. 2011.
Potyrailo et al., "RFID Sensors as the Common Sensing Platform for Single-Use Biopharmaceutical Manufacturing", Measurement Science and Technology, vol. No. 22, Issue No. 8, pp. 082001-1-082001-17, Jul. 15, 2011.
Wang et al., "Impedance Analysis for Lateral Field Excited Acoustic Wave Sensors", Sensors and Actuators B: Chemical, vol. No. 156, Issue No. 2, pp. 969-975, Aug. 2011.
Latif et al., "Conductometric Sensors for Monitoring Degradation of Automotive Engine Oil", Sensors, vol. No. 11, Issue No. 9, pp. 8611-8625, Sep. 5, 2011.
Potyrailo et al., "Materials and Transducers Toward Selective Wireless Gas Sensing", Chemical Reviews, vol. No. 111, Issue No. 11, pp. 7315-7354, Sep. 7, 2011.
Perez et al., "Low-Cost Oil Quality Sensor Based on Changes in Complex Permittivity", Sensors, vol. No. 11, Issue No. 11, pp. 10675-10690, Nov. 2011.

(56) References Cited

OTHER PUBLICATIONS

Potyrailo et al., "Multivariable Passive RFID Vapor Sensors: Pilot-Scale Manufacturing and Laboratory Evaluation", Future of Instrumentation International Workshop, pp. 1-2, Nov. 7-8, 2011.

Aghayan, "On-Line Monitoring of Engine Health through the Analysis of Contaminants in Engine Lubricant", The School of Graduate and Postdoctoral Studies, The University of Western Ontario, London, Ontario, Canada, pp. 1-273, 2012.

Potyrailo et al., "Multivariable MHz and GHz Wireless Chem/Bio Sensors for Environmental, Industrial, and Security Applications", The 14th International Meeting on Chemical Sensors, Nuremberg, Germany, pp. 399-402, May 20-23, 2012.

Vasilyeva et al., "Differences in Behaviour of Adsorbed Water in Kaolinites and Montmorillonites in Temperature Range from −90° C. to +140° C. by Dielectric Spectroscopy", Journal of Physics: Conference Series, vol. No. 394, Issue No. 1, pp. 012028-1-012028-6, 2012.

Datla et al., "Wireless Distributed Computing: A Survey of Research Challenges", IEEE Communications Magazine, vol. No. 50, Issue No. 1, pp. 144-152, Jan. 5, 2012.

Datla et al., "Wireless Distributed Computing in Cognitive Radio Networks", Ad Hoc Networks, vol. No. 10, Issue No. 05, pp. 845-857, Jul. 2012.

Fochtmann et al., "Optimization of the Lateral Field Excited Platform for Liquid Sensing Applications", Sensors and Actuators B: Chemical, vol. No. 170, pp. 95-103, Jul. 31, 2012.

Non-Final Rejection issued in connection with related U.S. Appl. No. 12/942,732 dated Feb. 7, 2013.

De Souza et al., "A Close Dielectric Spectroscopic Analysis of Diesel/Biodiesel Blends and Potential Dielectric Approaches for Biodiesel Content Assessment", Fuel, vol. No. 105, pp. 705-710, Mar. 2013.

Swiech et al., "Dielectric Properties of Synthetic Oil Sands", Society of Petroleum Engineers—SPE Heavy Oil Conference, Calgary, Alberta, Canada, vol. No. 1, pp. 1-11, Jun. 11-13, 2013.

Zhu et al., "Survey of Lubrication Oil Condition Monitoring, Diagnostics, and Prognostics Techniques and Systems", Journal of Chemical Science and Technology, vol. No. 2, Issue No. 3, pp. 100-115, Jul. 2013.

Agilent Impedance Measurement Handbook, "A Guide to Measurement Technology and Techniques", 4th Edition, Agilent Technologies, pp. 1-140, Sep. 10, 2013.

PCT Search Report and Written Opinion issued in connection with related PCT Application No. PCT/US2013/058932 dated Dec. 12, 2013.

Toledo et al., "Application of Quartz Tuning Forks and Extensional Microresonators for Viscosity and Density Measurements in Oil/Fuel Mixtures", Microsystem Technologies, vol. No. 20, Issue No. 4, pp. 945-953, Apr. 2014.

Elzagzoug et al., "Condition Monitoring of High Voltage Transformer Oils Using Optical Chromaticity", Measurement Science and Technology, vol. No. 25, Issue No. 6, pp. 065205-1-065205-9, Jun. 2014.

Soleimani et al., "Base Oil Oxidation Detection Using Novel Chemical Sensors and Impedance Spectroscopy Measurements", Sensors and Actuators B: Chemical, vol. No. 199, pp. 247-258, Aug. 2014.

Non-Final Rejection issued in connection with related U.S. Appl. No. 14/031,951 dated Sep. 2, 2014.

Hoja et al., "Miniaturized Impedance Analyzer Using AD5933", Lecture Notes on Impedance Spectroscopy, vol. No. 5, pp. 93-100, Feb. 17, 2015.

Chabowski et al., "Simple Wide Frequency Range Impedance Meter Based on AD5933 Integrated Circuit", Metrology and Measurement Systems, vol. No. 22, Issue No. 1, pp. 13-24, Mar. 15, 2015.

Simic, "Complex Impedance Measurement System for the Frequency Range from 5 kHz to 100 kHz", Key Engineering Materials, vol. No. 644, pp. 133-136, May 11, 2015.

Chen et al., "Novel Undercoupled Radio-Frequency (RF) Resonant Sensor for Gaseous Ethanol and Interferents Detection", Sensors and Actuators A: Physical, vol. No. 230, pp. 63-73, Jul. 1, 2015.

Ghaffari et al., "A Wireless Multi-Sensor Dielectric Impedance Spectroscopy Platform", Sensors, vol. No. 15, Issue No. 9, pp. 23572-23588, Sep. 17, 2015.

Wang et al., "Probe Improvement of Inductive Sensor for Online Health Monitoring of Mechanical Transmission Systems", IEEE Transactions on Magnetics, vol. No. 51, Issue No. 11, pp. 1-4, Nov. 2015.

Poseidon Systems, "Oil Quality Products", Trident QM1100; Trident QM2100; Trident WM800, pp. 1-3, Retrieved from http://www.poseidonsys.com/products/oil-quality on Dec. 24, 2015.

Tandelta Systems, "Oil Quality Sensor", Tandelta Oil Condition Monitoring, pp. 1-5, Retrieved from http://www.tandeltasystems.com/products/oil-quality-sensor-2/ on Dec. 24, 2015.

Zhu et al., "An Integrated Lubricant Oil Conditioning Sensor Using Signal Multiplexing", Journal of Micromechanics and Microengineering, vol. No. 25, Issue No. 1, pp. 015006-1-015006-12, Dec. 24, 2015.

Eurasian Search Report issued in connection with related EA Application No. 201592216 dated Aug. 4, 2016.

Non-Final Rejection issued in connection with related U.S. Appl. No. 14/710,299 dated Aug. 29, 2016.

Australian Examination Report issued in connection with related AU Application No. 2015268746 dated Oct. 21, 2016.

Dervos, C.T., "A complex permittivity bases sensor for the electrical characterization of high-voltage transformers oils," Sensors, vol. 5, pp. 302-316 (2005).

Zaretsky, M.C., "Moisture sensing in transformer oil using thin-film microdielectrometry," IEEE Transactions on Electrical Insulations, vol. 24, No. 6, pp. 1167-1176 (Dec. 1989).

Non-Final Rejection towards U.S. Appl. No. 14/585,690 dated Mar. 16, 2017.

Surman et al., filed Sep. 28, 2012, U.S. Appl. No. 13/630,587.
Surman et al., filed Sep. 28, 2012, U.S. Appl. No. 13/630,739.
Surman et al., filed May 2, 2014, U.S. Appl. No. 61/987,853.
Surman et al., filed Oct. 21, 2016, U.S. Appl. No. 15/305,664.
Potyrailo et al., filed Sep. 25, 2015, U.S. Appl. No. 14/866,320.
Potyrailo et al., filed Dec. 30, 2014, U.S. Appl. No. 14/585,690.
Potyrailo et al., filed Dec. 22, 2015, U.S. Appl. No. 62/271,030.
Potyrailo et al., filed Mar. 3, 2016, U.S. Appl. No. 15/060,193.

Bauerle, "Study of Solid Electrolyte Polarization by a Complex Admittance Method", Journal of Physics and Chemistry of Solids, vol. No. 30, Issue No. 12, pp. 2657-2670, Dec. 1969.

Matsui, "Complex-Impedance Analysis for the Development of Zirconia Oxygen Sensors", Solid State Ionics, vol. No. 3-4, pp. 525-529, Aug. 1981.

Persaud et al., "Analysis of Discrimination Mechanisms in the Mammalian Olfactory System Using a Model Nose", Nature, vol. No. 299, pp. 352-355, Sep. 23, 1982.

Sen et al., "The Frequency Dependent Dielectric and Conductivity Response of Sedimentary Rocks", Journal of Microwave Power, vol. No. 18, Issue No. 1, pp. 95-105, 1983.

Raythatha et al., "Dielectric Properties of Clay Suspensions in MHz to GHz Range", Journal of Colloid and Interface Science, vol. No. 109, Issue No. 2, pp. 301-309, Feb. 1986.

Ward et al., "In Situ Interfacial Mass Detection with Piezoelectric Transducers", Science, vol. No. 249, Issue No. 4972, pp. 1000-1007, Aug. 31, 1990.

Shi et al., "Capacitance-Based Instrumentation for Multi-Interface Level Measurement", Measurement Science and Technology, vol. No. 2, Issue No. 10, pp. 923-933, May 17, 1991.

Gutierrez et al., "Use of Complex Impedance Spectroscopy in Chemical Sensor Characterization", Sensors and Actuators B: Chemical, vol. No. 4, Issue No. 3-4, pp. 359-363, Jun. 1991.

Wise et al., "Microfabrication Techniques for Integrated Sensors and Microsystems", Science, vol. No. 254, pp. 1335-1342, Nov. 29, 1991.

Mullen et al., "Trace Detection of Ionic Species with Surface Enhanced Raman Spectroscopy", Spectroscopy, vol. No. 7, Issue No. 5, pp. 24-32, Jun. 1992.

(56) References Cited

OTHER PUBLICATIONS

Ervin et al., "Development of a Fiber-Optic Sensor for Trace Metal Detection in Aqueous Environments", Applied Optics, vol. No. 32, Issue No. 22, pp. 4287-4290, Aug. 1, 1993.
Agar et al., "Energy Absorption Probes Control Oily-Water Discharges", Hydrocarbon Processing, vol. No. 72, Issue No. 8, pp. 55-59, Aug. 1, 1993.
Wensink, "Dielectric Properties of Wet Soils in the Frequency Range 1-3000 MHz", Geophysical Prospecting, vol. No. 41, Issue No. 6, pp. 671-696, Aug. 1993.
Pal, "Techniques for Measuring the Composition (Oil and Water Content) of Emulsions—A state of the Art Review", Colloids and Surfaces: A Physicochemical and Engineering Aspects, vol. No. 84, Issue No. 2-3, pp. 141-193, May 11, 1994.
Garrouch et al., "The Influence of Clay Content, Salinity, Stress, and Wettability on the Dielectric Properties of Brine-Saturated Rocks: 10 Hz to 10 MHz", Geophysics, vol. No. 59, Issue No. 6, pp. 909-917, Jun. 1994.
Isaksen et al., "A Capacitance-Based Tomography System for Interface Measurement in Separation Vessels", Measurement Science and Technology, vol. No. 5, Issue No. 10, pp. 1262-1271, Jun. 9, 1994.
Yang et al., "A Multi-Interface Level Measurement System using a Segmented Capacitance Sensor for Oil Separators", Measurement Science and Technology, vol. No. 5, Issue No. 9, pp. 1177-1180, Jul. 19, 1994.
Garcia-Golding et al., "Sensor for Determining the Water Content of Oil-in-water Emulsion by Specific Admittance Measurement", Sensors and Actuators: A. Physical, vol. No. 47, Issue No. 1-3, pp. 337-341, Mar.-Apr. 1995.
Ghiotti et al., "Moisture Effects on Pure and Pd-Doped SnO2 Thick Films Analysed by FTIR Spectroscopy and Conductance Measurements", Sensors and Actuators B: Chemical, vol. No. 25, Issue No. 1-3, pp. 520-524, Apr. 1995.
Legin et al., "Development and Analytical Evaluation of a Multisensor System for Water Quality Monitoring", Sensors and Actuators B: Chemical, vol. No. 27, Issue No. 1-3, pp. 377-379, Jun. 1995.
Malinowska et al., "Enhanced Electrochemical Performance of Solid-State Ion Sensors Based on Silicone Rubber Membranes", The 8th International Conference on Solid-State Sensors and Actuators, and Eurosensors IX, Stockholm, Sweden, pp. 851-854, Jun. 25-29, 1995.
Amrani et al., "High-Frequency Measurements of Conducting Polymers: Development of a New Technique for Sensing Volatile Chemicals", Measurement Science and Technology, vol. No. 6, Issue No. 10, pp. 1500-1507, Jul. 20, 1995.
Hutzler et al., "Measurement of Foam Density Profiles Using AC Capacitance", Europhysics Letters, vol. No. 31, Issue No. 8, pp. 497-502, Sep. 10, 1995.
Nicolaou et al., "Radiofrequency Encoded Combinatorial Chemistry", Angewandte Chemie International Edition, vol. No. 34, Issue No. 20, pp. 2289-2291, Nov. 3, 1995.
Leff et al., "Synthesis and Characterization of Hydrophobic, Organically-Soluble Gold Nanocrystals Functionalized with Primary Amines", Langmuir, vol. No. 12, Issue No. 20, pp. 4723-4730, 1996.
Amrani et al., "Multi-Frequency Measurements of Organic Conducting Polymers for Sensing of Gases and Vapours", Sensors and Actuators B: Chemical, vol. No. 33, Issue No. 1-3, pp. 137-141, Jul. 1996.
Di Natale et al., "Multicomponent Analysis of Heavy Metal Cations and Inorganic Anions in Liquids by a Non-Selective Chalcogenide Glass Sensor Array", Sensors and Actuators B: Chemical, vol. No. 34, Issue No. 1-3, pp. 539-542, Aug. 1996.
Chinowsky et al., "Experimental Data from a Trace Metal Sensor Combining Surface Plasmon Resonance with Anodic Stripping Voltammetry", Sensors and Actuators B: Chemical, vol. No. 35, Issue No. 1-3, pp. 37-43, Sep. 1996.
Josse et al., "AC-Impedance-Based Chemical Sensors for Organic Solvent Vapors", Sensors and Actuators B: Chemical, vol. No. 36, Issue No. 1-3, pp. 363-369, Oct. 1996.
Santamarina et al., "Dielectric Permittivity of Soils Mixed With Organic and Inorganic Fluids (0.02GHz to 1.30 GHz)", Journal of Environmental and Engineering Geophysics, vol. No. 2, Issue No. 1, pp. 37-51, Mar. 1997.
Wang et al., "The Application of A.C. Impedance Technique for Detecting Glycol Contamination in Engine Oil", Sensors and Actuators B: Chemical, vol. No. 40, Issue No. 2-3, pp. 193-197, May 15, 1997.
Hammond et al., "An Acoustic Automotive Engine Oil Quality Sensor", International Conference on Solid-State Sensors and Actuators, Chicago, pp. 1343-1346, Jun. 16-19, 1997.
Amrani et al., "An Intelligent Gas Sensing System", Sensors and Actuators B: Chemical, vol. No. 44, Issue No. 1-3, pp. 512-516, Oct. 1997.
Di Natale et al., "Multicomponent Analysis on Polluted Waters by Means of an Electronic Tongue", Sensors and Actuators B: Chemical, vol. No. 44, Issue No. 1-3, pp. 423-428, Oct. 1997.
Vlasov et al., "Cross-Sensitivity Evaluation of Chemical Sensors for Electronic Tongue: Determination of Heavy Metal Ions", Sensors and Actuators B: Chemical, vol. No. 44, Issue No. 1-3, pp. 532-537, Oct. 1997.
Ehret et al., "On-line Control of Cellular Adhesion with Impedance Measurements Using Interdigitated Electrode Structures", Medical & Biological Engineering & Computing, vol. No. 36, Issue No. 3, pp. 365-370, May 1998.
Wohltjen et al., "Colloidal Metal-Insulator—Metal Ensemble Chemiresistor Sensor", Analytical Chemistry, vol. No. 70, Issue No. 14, pp. 2856-2859, Jul. 15, 1998.
Jaworski et al., "A Capacitance Probe for Interface Detection in Oil and Gas Extraction Plant", Measurement of Science and Technology, vol. No. 10, Issue No. 3, pp. L15-L20, Jan. 1999.
Homola et al., "Surface Plasmon Resonance Sensors: Review", Sensors and Actuators B: Chemical, vol. No. 54, Issue No. 1-2, pp. 3-15, Jan. 25, 1999.
Amrani et al., "Multi-Frequency Interrogation Technique Applied to Conducting Polymer Gas and Odour Sensors", IEE Proceedings—Science, Measurement and Technology, vol. No. 146, Issue No. 2, pp. 95-101, Mar. 1999.
Ishida et al., "Effects of pH on Dielectric Relaxation of Montmorillonite, Allophane, and Imogolite Suspensions", Journal of Colloid and Interface Science, vol. No. 212, Issue No. 1, pp. 152-161, Apr. 1, 1999.
Asskildit et al., "New Measuring Sensor for Level Detection in Subsea Separators", ABB Review, pp. 11-17, Apr. 1999.
Schuller et al., "Advanced Profile Gauge for Multiphase Systems", 1st World Congress on Industrial Process Tomography, Buxton, Greater Manchester, pp. 126-132, Apr. 14-17, 1999.
Legin et al., "The Features of the Electronic Tongue in Comparison with the Characterstics of the Discrete Ion-Selective Sensors", Sensors and Actuators B: Chemical, vol. No. 58, Issue No. 1-3, pp. 464-468, Sep. 21, 1999.
Artmann, "Electronic Identification Systems: State of the Art and their Further Development", Computers and Electronics in Agriculture, vol. No. 24, Issue No. 1-2, pp. 5-26, Nov. 1999.
Chyan et al., "Ultrapure Water Quality Monitoring by a Silicon-Based Potentiometric Sensor", Analyst, vol. No. 125, Issue No. 1, pp. 175-178, 2000.
Basu et al., "Smart Sensing" of Oil Degradation and Oil Level Measurements in Gasoline Engines, SAE 2000 World Congress, Detroit, Michigan, 2000-01-1366, pp. 1-7, Mar. 6-9, 2000.
Jurs et al., "Computational Methods for the Analysis of Chemical Sensor Array Data from Volatile Analytes", Chemical Reviews, vol. No. 100, Issue No. 7, pp. 2649-2678, Jun. 7, 2000.
McQuade et al., "Conjugated Polymer-Based Chemical Sensors", Chemical Reviews, vol. No. 100, Issue No. 7, pp. 2537-2574, Jun. 9, 2000.
Vlasov et al., "«Electronic Tongue»—New Analytical Tool for Liquid Analysis on the basis of Non-Specific Sensors and Methods of Pattern Recognition", Sensors and Actuators B: Chemical, vol. No. 65, Issue No. 1-3, pp. 235-236, Jun. 30, 2000.
Rakow et al., "A Colorimetric Sensor Array for Odour Visualization", Nature, vol. No. 406, pp. 710-713, Aug. 17, 2000.

(56) References Cited

OTHER PUBLICATIONS

Taton et al., "Scanometric DNA Array Detection with Nanoparticle Probes", Science, vol. No. 289, Issue No. 5485, pp. 1757-1760, Sep. 8, 2000.
Kaya, "Electrical Spectroscopy of Kaolin and Bentonite Slurries", Turkish Journal of Engineering and Environmental Sciences, vol. No. 25, pp. 345-354, 2001.
Lee, "Increase Oil Production and Reduce Chemical Usage through Separator Level Measurement by Density Profiling", ISA TECH/EXPO Technology Update Conference Proceedings, vol. No. 416, pp. 321-328, 2001.
Foster et al., "Detection of Trace Levels of Water in Oil by Photoacoustic Spectroscopy", Sensors and Actuators B: Chemical, vol. No. 77, Issue No. 3, pp. 620-624, Jul. 10, 2001.
MacDiarmid, ""Synthetic Metals": A Novel Role for Organic Polymers (Nobel Lecture)", Angewandte Chemie International Edition, vol. No. 40, Issue No. 14, pp. 2581-2590, Jul. 16, 2001.
Shirakawa, "The Discovery of Polyacetylene Film: The Dawning of an Era of Conducting Polymers", Angewandte Chemie International Edition, vol. No. 40, Issue No. 14, pp. 2575-2580, Jul. 16, 2001.
Ong et al., "Design and Application of a Wireless, Passive, Resonant-Circuit Environmental Monitoring Sensor", Sensors and Actuators A: Physical, vol. No. 93, Issue No. 1, pp. 33-43, Aug. 25, 2001.
Mourzina et al., "Development of Multisensor Systems based on Chalcogenide Thin Film Chemical Sensors for the Simultaneous Multicomponent Analysis of Metal Ions in Complex Solutions", Electrochimica Acta, vol. No. 47, Issue No. 1-2, pp. 251-258, Sep. 1, 2001.
Gawad et al., "Micromachined Impedance Spectroscopy Flow Cytometer for Cell Analysis and Particle Sizing", Lab on a Chip, vol. No. 1, Issue No. 1, pp. 76-82, Sep. 2001.
Heeger, "Semiconducting and Metallic Polymers: The Fourth Generation of Polymeric Materials", The Journal of Physical Chemistry B, vol. No. 105, Issue No. 36, pp. 8475-8491, Sep. 13, 2001.
Foster-Mills et al., "Photoacoustic Spectroscopy Detects Water in Oil", Sensors Online, pp. 1-5, Oct. 2001, Retrieved from http://archives.sensorsmag.com/articles/1001/12/pf_main.shtml on Apr. 11, 2016.
Janata, "Electrochemical Sensors and their Impedances: A Tutorial", Critical Reviews in Analytical Chemistry, vol. No. 32, Issue No. 2, pp. 109-120, 2002.
Harpster et al., "A Passive Humidity Monitoring System for in Situ Remote Wireless Testing of Micropackages", Microelectromechanical Systems, vol. No. 11, Issue No. 1, pp. 61-67, Feb. 2002.
Akyildiz et al., "Wireless Sensor Networks: A Survey", Computer Networks, vol. No. 38, Issue No. 4, pp. 393-422, Mar. 15, 2002.
Grimes et al., "Wireless Magnetoelastic Resonance Sensors: A Critical Review", vol. No. 2, Issue No. 7, pp. 294-313, Jul. 23, 2002.
Haes et al., "A Nanoscale Optical Biosensor: Sensitivity and Selectivity of an Approach Based on the Localized Surface Plasmon Resonance Spectroscopy of Triangular Silver Nanoparticles", Journal of the American Chemical Society, vol. No. 124, Issue No. 35, pp. 10596-10604, Aug. 8, 2002.
Ceresa et al., "Rational Design of Potentiometric Trace Level Ion Sensors. A Ag+-Selective Electrode with a 100 ppt Detection Limit", Analytical Chemistry, vol. No. 74, Issue No. 16, pp. 4027-4036, Aug. 15, 2002.
Alary et al.,"Subsea Water Separation: A Cost-Effective Solution for Ultra Deep Water Production", 17th World Petroleum Congress, Rio De Janeiro, Brazil, pp. 47-54, Sep. 1-5, 2002.
Smiechowski et al., "Electrochemical Monitoring of Water-Surfactant Interactions in Industrial Lubricants", Journal of Electroanalytical Chemistry, vol. No. 534, Issue No. 2, pp. 171-180, Oct. 18, 2002.
Butler et al., "Wireless, Passive, Resonant-Circuit, Inductively Coupled, Inductive Strain Sensor", Sensors and Actuators A: Physical, vol. No. 102, Issue No. 1, pp. 61-66, Dec. 1, 2002.
Janata et al., "Conducting Polymers in Electronic Chemical Sensors", Nature Materials, vol. No. 2, pp. 19-24, Jan. 2003.

Johns et al., "Sensitive Indirect Photometric Detection of Inorganic and Small Organic Anions by Capillary Electrophoresis Using Orange G as a Probe Ion", Electrophoresis, vol. No. 24, Issue No. 3, pp. 557-566, Jan. 2003.
Potyrailo et al., "Fluorescence Spectroscopy and Multivariate Spectral Descriptor Analysis for High-Throughput Multiparameter Optimization of Polymerization Conditions of Combinatorial 96-Microreactor Arrays", Journal of Combinatorial Chemistry, vol. No. 5, Issue No. 1, pp. 8-17, Jan.-Feb. 2003.
Fauveau et al., "Guided-Wave Radar Helps Level-Detection in Harsh Settings", Control Engineering, vol. No. 50, Issue No. 3, pp. 16, Mar. 1, 2003.
Grate et al., "Sorptive Behavior of Monolayer-Protected Gold Nanoparticle Films: Implications for Chemical Vapor Sensing", Analytical Chemistry, vol. No. 75, Issue No. 8, pp. 1868-1879, Apr. 15, 2003.
De Borba et al., "Determination of Sodium at Low NG/L Concentrations in Simulated Power Plant Waters by Ion Chromatography", Journal of Chromatography A, vol. No. 995, Issue No. 1-2, pp. 143-152, May 2, 2003.
Sakharov et al., "Liquid Level Sensor Using Ultrasonic Lamb Waves", Ultrasonics, vol. No. 41, Issue No. 4, pp. 319-322, Jun. 2003.
Kumar et al., "Investigation into the Interaction between Surface-Bound Alkylamines and Gold Nanoparticles", Langmuir, vol. No. 19, Issue No. 15, pp. 6277-6282, Jun. 25, 2003.
Mabic et al., "Adjusting the Quality of Treated Water to Experimental Detection Limits", GIT Labor-Journal, vol. No. 47, pp. 724-727, Jul. 2003.
Finkenzeller, "RFID Handbook: Fundamentals and Applications in Contactless Smart Cards and Identification", John Wiley & Sons, Ltd, Second Edition, pp. 1-427, Jul. 21, 2003.
Pasquale, "Mechanical Sensors and Actuators", Sensors and Actuators, A: Physical, vol. No. 106, Issue No. 1-3, pp. 142-148, Sep. 15, 2003.
Chopra et al., "Selective Gas Detection Using a Carbon Nanotube Sensor", Applied Physics Letters, vol. No. 83, Issue No. 11, pp. 2280-2282, Sep. 15, 2003.
Bauer et al., "Resonant Nanocluster Technology-From Optical Coding and High Quality Security Features to Biochips", Nanotechnology, vol. No. 14, Issue No. 12, pp. 1289-1311, Nov. 4, 2003.
Wang et al., "A New Technique for Detecting Antifreeze in Engine Oil During Early Stage of Leakage", Sensors and Actuators B: Chemical, vol. No. 96, Issue No. 1-2, pp. 157-164, Nov. 15, 2003.
Briglin et al., "Detection of Organic Mercaptan Vapors using Thin Films of Alkylamine-Passivated Gold Nanocrystals", Langmuir, vol. No. 20, Issue No. 2, pp. 299-305, Jan. 20, 2004.
Shamsipur et al., "New Macrocyclic Diamides as Neutral Ionophores for Highly Selective and Sensitive PVC-Membrane Electrodes for Be2+ Ion", Electroanalysis, vol. No. 16, Issue No. 4, pp. 282-288, Mar. 2004.
Joseph et al., "Chemiresistor Coatings from Pt- and Au-Nanoparticle/Nonanedithiol Films: Sensitivity to Gases and Solvent Vapors", Sensors and Actuators B: Chemical, vol. No. 98, Issue No. 2-3, pp. 188-195, Mar. 15, 2004.
Seyfried et al., "Measurement of Soil Water Content with a 50-MHz Soil Dielectric Sensor", Soil Science Society of America, vol. No. 68, Issue No. 2, pp. 394-403, Mar.-Apr. 2004.
Fransen, "New Control System Detects Desalter Problems before Upsets Occur", Agar Corporation, Prepared for Presentation at the AICHE 2004 Spring National Meeting, pp. 1-7, Apr. 2004.
Want et al., "Enabling Ubiquitous Sensing with RFID", Computer, vol. No. 37, Issue No. 4, pp. 84-86, Apr. 2004.
Bennett et al., "Monitoring the Operation of an Oil/Water Separator using Impedance Tomography", Minerals Engineering, vol. No. 17, Issue No. 5, pp. 605-614, May 2004.
Varma et al., "High-Speed Label-Free Detection by Spinning-Disk Micro-Interferometry", Biosensors and Bioelectronics, vol. No. 19, Issue No. 11, pp. 1371-1376, Jun. 15, 2004.
Ikenishi et al., "The Dielectric Characteristics of Agricultural Land for On-site and Real Time Measurement", SICE Annual Conference, Sapporo, Japan, vol. No. 2, pp. 1489-1492, Aug. 4-6, 2004.

(56) References Cited

OTHER PUBLICATIONS

Pavlov et al., "Aptamer-Functionalized Au Nanoparticles for the Amplified Optical Detection of Thrombin", Journal of the American Chemical Society, vol. No. 126, Issue No. 38, pp. 11768-11769, Sep. 3, 2004.
Thomas et al., "Conjugated Polymer Sensors: Design Principles Towards Enhanced Versatility", pp. 1-6, Dec. 2004.
Buhrdorf et al., "Multiparameteric Oil Condition Sensor Based on the Tuning Fork Technology for Automotive Applications", Advanced Microsystems for Automotive Applications, pp. 289-298, 2005.
Holstad et al., "Scattered Gamma Radiation Utilized for Level Measurements in Gravitational Separators", IEEE Sensors, vol. No. 5, Issue No. 2, pp. 175-182, Apr. 2005.
Rose et al., "Sensitivity Gains in Chemosensing by Lasing Action in Organic Polymers", Nature, vol. No. 434, pp. 876-879, Apr. 14, 2005.
Jaworski et al., "Measurements of Oil-Water Separation Dynamics in Primary Separation Systems Using Distributed Capacitance Sensors", Flow Measurement and Instrumentation, vol. No. 16, Issue No. 2-3, pp. 113-127, Apr.-Jun. 2005.
Josh et al., "Broadband Electrical Properties of Clays and Shales: Comparative Investigations of Remolded and Preserved Samples", Geophysics, vol. No. 80, Issue No. 2, pp. D129-D143, Mar.-Apr. 2015.
PCT Search Report issued in connection with related PCT Application No. PCT/US2016/067885 dated Apr. 4, 2017.
Cheryl Margaret Surman et al., filed Oct. 21, 2016, U.S. Appl. No. 15/305,664.
Radislav Alexandrovich Potyrailo et al., filed Dec. 30, 2014, U.S. Appl. No. 14/585,690.
Cheryl Margaret Surman et al., filed Sep. 28, 2012, U.S. Appl. No. 13/630,587.
Cheryl Margaret Surman et al., filed Dec. 22, 2015, U.S. Appl. No. 62/271,030.
Office Action issued for Russian Application No. 2015109373/28, dated Nov. 27, 2017.
Decision to Grant issued for Russian Application No. 2015109373/28, dated Feb. 16, 2018.
Office Action issued for Indonesian Application No. P00201501807, dated Jul. 16, 2019.
Communication Pursuant to Article 94(3) EPC, issued for European Application No. 13770995.2, dated Nov. 30, 2018, 5 pages.
Communication Pursuant to Article 94(3) EPC, issued for European Application No. 15720550.1, dated May 14, 2018, 6 pages.
Communication Pursuant to Article 94(3) EPC, issued for European Application No. 13763425.9, dated Feb. 6, 2019, 3 pages.
Technical Report, relating to Brazilian Application No. BR112015006097-8, dated Oct. 3, 2019.
Technical Report, relating to Brazilian Application No. BR112015005324-6, dated Nov. 28, 2019.

\* cited by examiner

SENSOR SYSTEMS FOR MEASURING AN INTERFACE LEVEL IN A MULTI-PHASE FLUID COMPOSITION

RELATED APPLICATIONS

This application claims the benefit of U.S. provisional application 61/987,853 filed on May 2, 2014 and is a continuation in part of U.S. application Ser. No. 13/630,587 and U.S. application Ser. No. 13/630,739, both filed on Sep. 28, 2012 by General Electric Company, all of which are incorporated herein by reference.

FIELD

The subject matter disclosed herein generally relates to sensors, and more particularly to level sensors to determine the interface level of a multi-phase fluid composition.

BACKGROUND

Measurement of the composition of emulsions and the interface level of immiscible fluids is important in many applications. For example, it is important to characterize emulsions in oil field management. The measurement of the water and oil content of emulsions from individual oil wells may vary over the life of an oil field and may indicate the overall health of a field. In the case of injection wells, it is critical to control water quality to reduce hydrate formation and corrosion. Characterization of the composition of the oil and water mixture (e.g., measurement of the relative proportions of oil and water in the mixture) helps the operator improve well productivity and capacity. The information obtained is also useful to reduce back-pressure of wells, flowline size and complexity, and thermal insulation requirements.

Characterization of emulsions is also important in the operation of systems that contain fluids in a vessel (vessel systems) such as fluid processing systems. Vessel systems may include storage tanks, reactors, separators and desalters. Vessel systems are used in many industries and processes, such as the oil and gas, chemical, pharmaceutical, food processing industries, among others. For example, separation of water from raw oil is important to establishing production streams of oil and gas. Crude oil leaving the wellhead is both sour (contains hydrogen sulfide gas) and wet (contains water). The crude leaving the wellhead must be processed and treated to make it economically viable for storage, processing and export. One way of treating the raw oil is through the use of a separator. Most separators are driven by gravity and use the density differences between individual fluid phases of oil, water, gas, and solids to accomplish the separation. Identification of the interface levels of these layers is critical to the control of the separation process. Another fluid processing system where characterization of emulsions and measurement of the interface level is important is a desalter. Desalters are used in a refinery to control overhead corrosion downstream. In a desalter water and crude oil are mixed, inorganic salts are extracted into the water, and water is then separated and removed.

Finally, it is important to accurately characterize the water and salinity in the crude oil itself at various stages of the life of the product from a cost standpoint. Oil is a valuable commodity and underestimation of the water content in a typical tanker load can have significant cost consequences.

Wastewater management is another application where measurement and characterization of emulsion is important. Large quantities of oily wastewater are generated in the petroleum industry from both recovery and refining. A key factor in controlling the oil discharge concentrations in wastewater is improved instrumentation for monitoring the oil content of emulsions.

Many types of level and interface instruments have been contemplated over the years and a subset of those have been commercialized. Among those are gamma-ray sensors, guided wave sensors, magnetostrictive sensors, microwave sensors, ultrasonic sensors, single plate capacitance/admittance sensors, segmented capacitance sensors, inductive sensors, and computed tomography sensors. Each of the sensors has advantages and disadvantages. Some of the sensors are prohibitively expensive for many users. Some of the sensors may require a cooling jacket to perform at operating temperatures (above 125° C.). Some interface instruments require a clear interface to work, which can be problematic when working with diffuse emulsions. Some are susceptible to fouling. Other sensors do not have the ability to provide a profile of the tank, but rather monitor discreet points in the desalting process. Systems using electrodes are susceptible to the shorting of electrodes in high salinity applications and are susceptible to fouling. Finally, many of these systems are complex and difficult to implement.

Some existing sensor systems have used individual capacitive elements to measure fluid levels. A key limitation of those sensor systems is their inability to simultaneously quantify several components in the liquid. Capacitance methods have been used to measure dielectric constant of a liquid using specially designed electrodes for capacitance measurements. These designs are limited by the need for separate types of electrodes for capacitance measurements and for conductivity measurements. Inductor capacitor circuits also have been used to monitor the fluid level in a container using an electromagnetic resonator where change in capacitance was related to fluid level and fluid type. However, it has been the consensus of those of ordinary skill in the art that the filling of the resonator by a conducting liquid increased the uncertainties and noise in measurements by about one order of magnitude as compared to the values in a non-conducting fluid such as in air. However, these methods do not provide accurate measurements of concentrations of individual analytes at the limits of their minimum and maximum concentrations in the mixture.

With existing sensor systems, no one system is capable of delivering a combination of low cost, high sensitivity, favorable signal-to-noise ratio, high selectivity, high accuracy, and high data acquisition speeds. Additionally no existing system has been described as capable of accurately characterizing or quantifying fluid mixtures where one of the fluids is at a low concentration (i.e. at their minimum and maximum limits).

SUMMARY OF THE INVENTION

The disclosure provides an alternative to the expense, reliability and accuracy problems of existing level sensor systems. An electrically resonant transducer (resonant transducer) may provide one or more of low cost, high sensitivity, favorable signal-to-noise ratio, high selectivity, high accuracy, and high data acquisition speeds. The resonant transducer is incorporated in a robust sensor without the need for a clear interface. The disclosure also provides a sensor that may be less susceptible to fouling, particularly in applications involving emulsions.

This disclosure describes, among other things, a sensor having a sampling cell, a bottom winding disposed around the sampling cell, and a top winding disposed around the bottom winding. Preferably, the sampling cell comprises a tube or other structure adapted to locate a stationary or flowing fluid, for example oil or water.

In accordance with one exemplary non-limiting embodiment, the disclosure relates to a sensor having a resonant transducer configured to determine a composition of an emulsion or other dispersion and includes a sampling assembly and an impedance analyzer.

In another embodiment, the disclosure relates to a system including a fluid processing system; a fluid sampling assembly; and a resonant sensor system coupled to the fluid sampling assembly.

In another embodiment, the disclosure relates to a method for measuring a level of a mixture of fluids in a vessel. The method includes the steps of detecting a signal from a resonant sensor system at a plurality of locations in the vessel; converting each signal to values of the complex impedance spectrum for the plurality of locations; storing the values of the complex impedance spectrum and frequency values; and determining a fluid phase inversion point from the values of the complex impedance spectrum.

In another embodiment, the disclosure relates to a method for determining a composition of a mixture of oil and water in a vessel. The method includes the step of determining values of the complex impedance spectrum of the mixture of oil and water as a function of a height in the vessel with a resonant transducer. The method also includes the step of determining a fluid phase inversion point from the values of the complex impedance spectrum; applying an oil phase model to the values of the complex impedance spectrum and conductivity values above the fluid phase inversion point, and applying a water phase model to the values of the complex impedance spectrum below the fluid phase inversion point.

In another embodiment, the disclosure relates to a sensor comprising a resonant transducer configured to simultaneously determine concentration of a first and a second component of an emulsion.

In another embodiment, the disclosure relates to a sensor having a resonant transducer configured to determine a composition of an emulsion.

In another embodiment, the disclosure relates to a sensor system having a resonant transducer configured to determine a composition of an emulsion. The sensor system includes a sampling assembly and an impedance analyzer.

In another embodiment, the disclosure relates to a method for determining a composition of a mixture of a first fluid and a second fluid in a vessel. The determination of the composition is accomplished by determining, with a sensor system, a set of complex impedance spectrum values of the mixture of the first fluid and the second fluid as a function of a height in the vessel. The method includes the step of determining a fluid phase inversion point from the set of complex impedance spectrum values. The method also includes the steps of applying a phase model of the first fluid to the set of complex impedance spectrum values above the fluid phase inversion point, and applying a phase model of the second fluid to the set of complex impedance spectrum values below the fluid phase inversion point.

BRIEF DESCRIPTION OF THE FIGURES

Other features and advantages of the present disclosure will be apparent from the following more detailed description of the preferred embodiment, taken in conjunction with the accompanying drawings which illustrate, by way of example, the principles of certain aspects of the disclosure.

DETAILED DESCRIPTION

Figure 1:
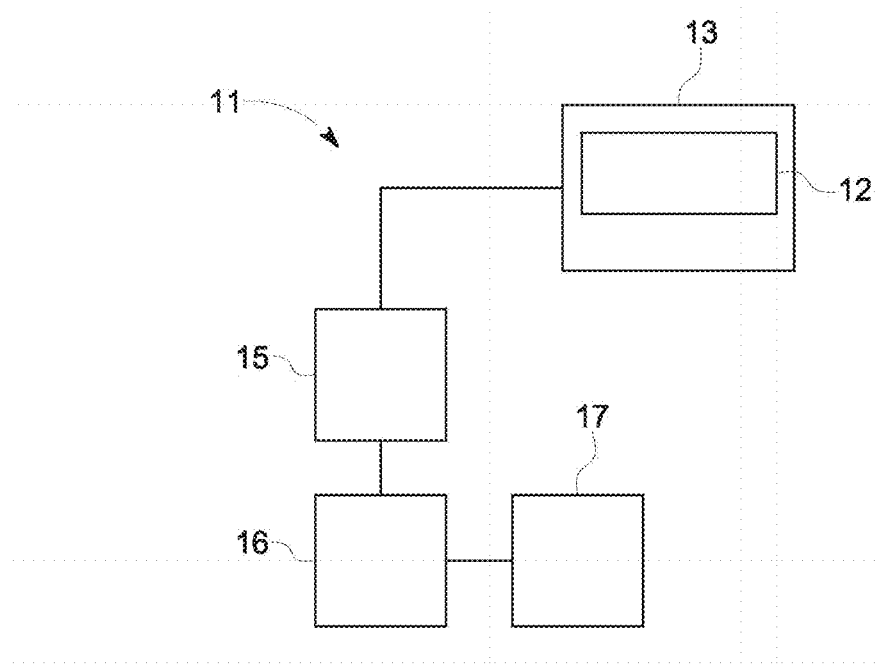
FIG. 1 is a schematic of a non-limiting embodiment of a resonant sensor system.

As discussed in detail below, embodiments of the present invention provide systems for, among other things, reliably and accurately measuring the fluid level in a fluid processing vessel. A resonant sensor system provides effective and accurate measurement of the level of the transition or emulsion layer through the use of a resonant transducer such as an inductor-capacitor-resistor structure (LCR) multivariable resonant transducer and the application of multivariate data analysis applied to the signals from the transducer. The resonant sensor system also provides the ability to determine the composition of water and oil mixtures, oil and water mixtures and, where applicable, the emulsion layer.

The resonant transducer includes a resonant circuit and a pick up coil. The electrical response of the resonant transducer immersed in a fluid is translated into simultaneous changes to a number of parameters. These parameters may include the complex impedance response, resonance peak position, peak width, peak height and peak symmetry of the impedance response of the sensor antenna, magnitude of the real part of the impedance, resonant frequency of the imaginary part of the impedance, antiresonant frequency of the imaginary part of the impedance, zero-reactance frequency, phase angle, and magnitude of impedance, and others as described in the definition of the term sensor "spectral parameters." These spectral parameters may change depending upon the dielectric properties of the surrounding fluids. The typical configuration of a resonant transducer may include an LCR resonant circuit and an antenna. The resonant transducer may operate with a pickup coil connected to the detector reader (impedance analyzer) where the pickup coil provides excitation of the transducer and detection of the transducer response. The resonant transducer may also operate when the excitation of the transducer and detection transducer response is performed when the transducer is directly connected to the detector reader (impedance analyzer).

A resonant transducer may offer one or more of high sensitivity, favorable signal-to-noise ratio, high selectivity, high accuracy, and high data acquisition speeds in a robust sensor without the need for optical transparency of the analyzed fluid and the measurement flow path. Instead of conventional impedance spectroscopy that scans across a wide frequency range (from a fraction of Hz to tens of MHz or GHz) a resonant transducer is used to acquire a spectrum rapidly and with high signal-to-noise across only a narrow frequency range. The sensing capability is enhanced by putting the sensing region between the electrodes that constitute a resonant circuit. As implemented in a fluid processing system such as a desalter or a separator, the resonant sensor system may include a sampling assembly and a resonant transducer coupled to the fluid sampling assembly. The resonant sensor system implements a method for measuring the level of a mixture of fluids in a vessel, and may also implement a method for determining the composition of a mixture of oil and water in a vessel. The resonant transducers may be capable of accurately quantifying individual analytes at their minimum and maximum limits. The resonant sensor system may be able to determine the composition of fluid mixtures even when one of the fluids is at a low concentration.

Nonlimiting examples of fluid processing systems include reactors, chemical reactors, biological reactors, storage vessels, containers, and others known in the art.

Illustrated in FIG. 1 is a schematic of an embodiment of a resonant sensor system 11. The resonant sensor system 11 includes a resonant transducer 12, a sampling assembly 13, and an impedance analyzer (analyzer 15). The analyzer 15 is coupled to a processor 16 such as a microcomputer. Data received from the analyzer 15 is processed using multivariate analysis, and the output may be provided through a user interface 17. Analyzer 15 may be an impedance analyzer that measures both amplitude and phase properties and correlates the changes in impedance to the physical parameters of interest. The analyzer 15 scans the frequencies over the range of interest (i.e., the resonant frequency range of the LCR circuit) and collects the impedance response from the resonant transducer 12.

Figure 2:
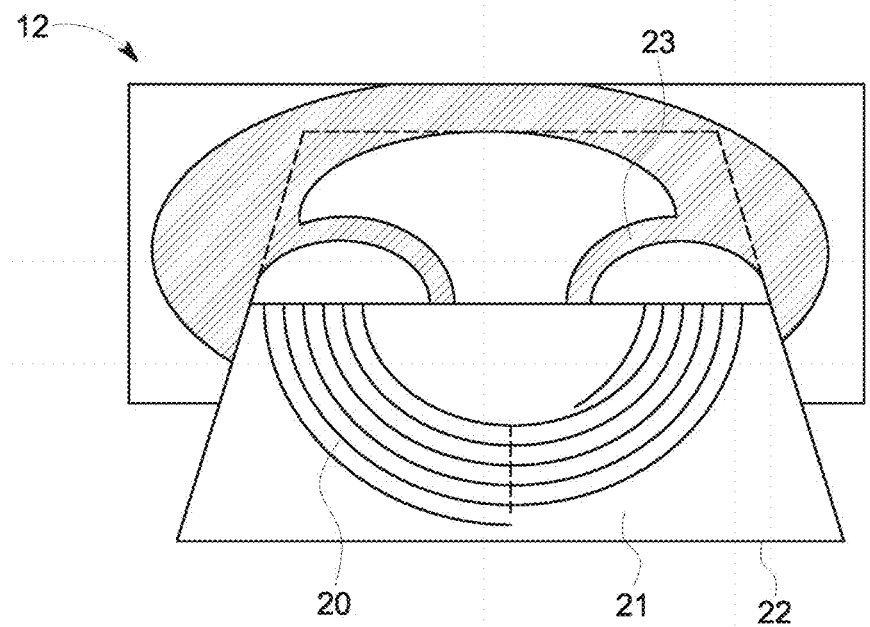
FIG. 2 is a non-limiting illustration of the operation of a resonant transducer.

As shown in FIG. 2, resonant transducer 12 includes an antenna 20 disposed on a substrate 22. The resonant transducer may be separated from the ambient environment with a dielectric layer 21. In some embodiments, the thickness of the dielectric layer 21 may range from 2 nm to 50 cm, more specifically from 5 nm to 20 cm; and even more specifically from 10 nm to 10 cm. In some applications the resonant transducer 12 may include a sensing film deposited onto the transducer. In response to environmental parameters an electromagnetic field 23 may be generated in the antenna 20 that extends out from the plane of the resonant transducer 12. The electromagnetic field 23 may be affected by the dielectric property of an ambient environment providing the opportunity for measurements of physical parameters. The resonant transducer 12 responds to changes in the complex permittivity of the environment. The real part of the complex permittivity of the fluid is referred to as a "dielectric constant". The imaginary part of the complex permittivity of the fluid is referred to as a "dielectric loss factor". The imaginary part of the complex permittivity of the fluid is directly proportional to conductivity of the fluid.

Measurements of fluids can be performed using a protecting layer that separates the conducting medium from the antenna 20. Response of the resonant transducer 12 to the composition of the fluids may involve changes in the dielectric and dimensional properties of the resonant transducer 12. These changes are related to the analyzed environment that interacts with the resonant transducer 12. The fluid-induced changes in the resonant transducer 12 affect the complex impedance of the antenna circuit through the changes in material resistance and capacitance between the antenna turns.

Figure 3:
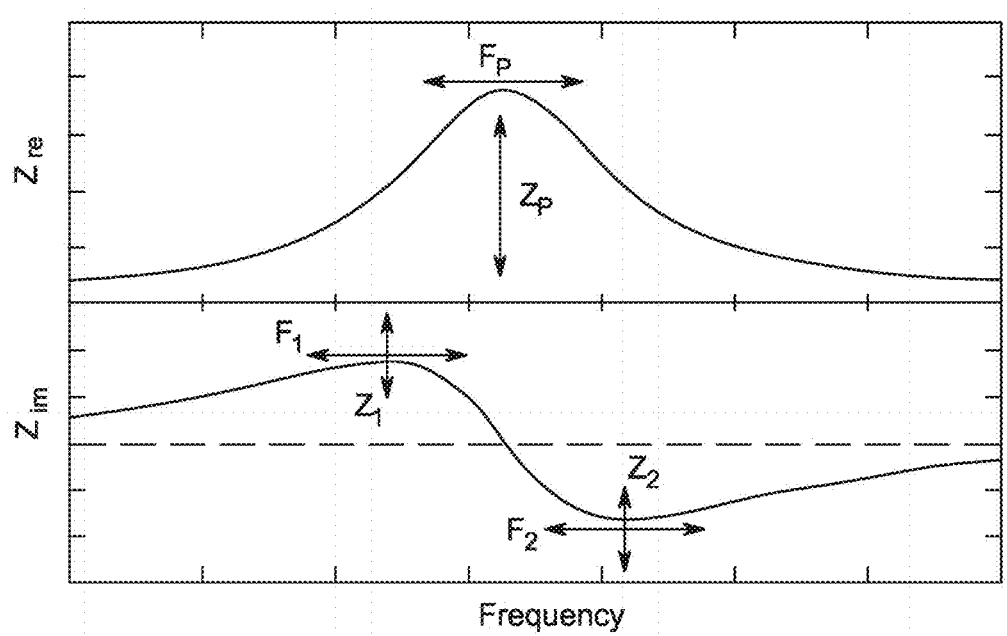
FIG. 3 is an example of a measured complex impedance spectrum used for multivariate analysis.

For selective fluid characterization using a resonant transducer 12, the complex impedance spectra of the sensor antenna 20 are measured as shown in FIG. 3. At least three data points of impedance spectra of the emulsion are measured. Better results may be achieved when at least five data points of the impedance spectra of the emulsion are measured. Non limiting examples of number of measured data points are 8, 16, 32, 64, 101, 128, 201, 256, 501, 512, 901, 1024, 2048 data points. Spectra may be measured as a real part of impedance spectra or an imaginary part of impedance spectra or both parts of impedance spectra. Non-limiting examples of LCR resonant circuit parameters include impedance spectrum, real part of the impedance spectrum, imaginary part of the impedance spectrum, both real and imaginary parts of the impedance spectrum, frequency of the maximum of the real part of the complex impedance (Fp), magnitude of the real part of the complex impedance (Zp), resonant frequency (F 1) and its magnitude (Z 1) of the imaginary part of the complex impedance, and anti-resonant frequency (F 2) and its magnitude (Z 2) of the imaginary part of the complex impedance.

Additional parameters may be extracted from the response of the equivalent circuit of the resonant transducer 12. Non-limiting examples of the resonant circuit parameters may include quality factor of resonance, zero-reactance frequency, phase angle, and magnitude of impedance of the resonance circuit response of the resonant transducer 12. Applied multivariate analysis reduces the dimensionality of the multi-variable response of the resonant transducer 12 to a single data point in multidimensional space for selective quantitation of different environmental parameters of interest. Non-limiting examples of multivariate analysis tools are canonical correlation analysis, regression analysis, nonlinear regression analysis, principal components analysis, discriminate function analysis, multidimensional scaling, linear discriminate analysis, logistic regression, and/or neural network analysis. By applying multivariate analysis of the full complex impedance spectra or the calculated spectral parameters, quantitation of analytes and their mixtures with interferences may be performed with a resonant transducer 12. Besides measurements of the complex impedance spectra parameters, it is possible to measure other spectral parameters related to the complex impedance spectra. Examples include, but are not limited to, S-parameters (scattering parameters) and Y-parameters (admittance parameters). Using multivariate analysis of data from the sensor, it is possible to achieve simultaneous quantitation of multiple parameters of interest with a single resonant transducer 12.

A resonant transducer 12 may be characterized as one-dimensional, two-dimensional, or three-dimensional. A one-dimensional resonant transducer 12 may include two wires where one wire is disposed adjacent to the other wire and may include additional components.

Figure 4:
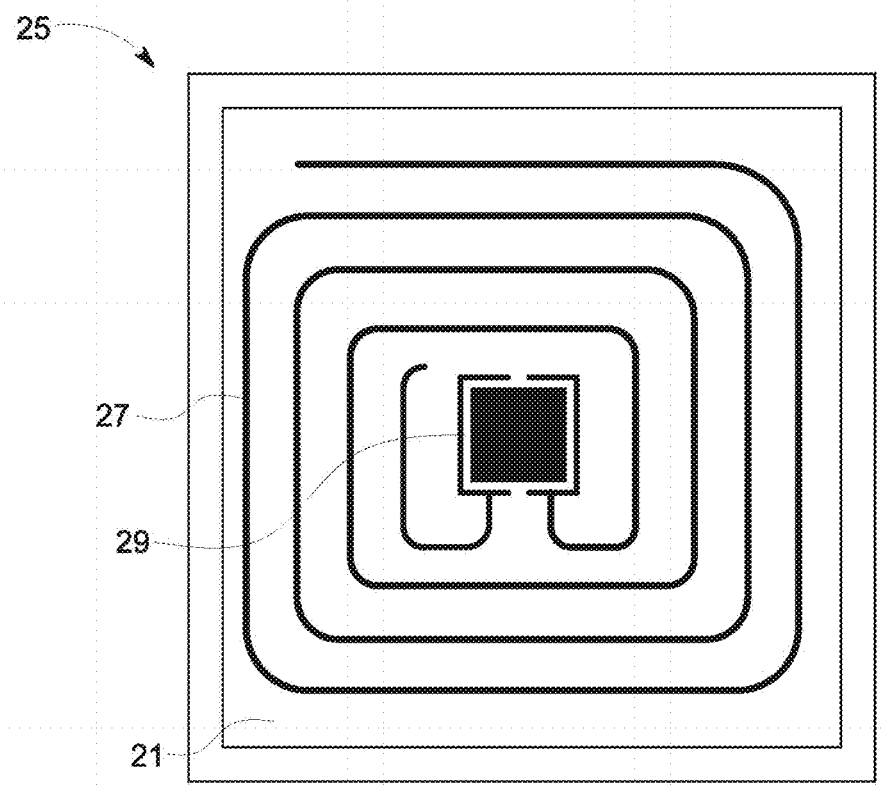
FIG. 4 illustrates an embodiment of a two-dimensional resonant transducer.

Shown in FIG. 4 is a two-dimensional resonant transducer 25 having a transducer antenna 27. The two-dimensional resonant transducer 25 is a resonant circuit that includes an LCR circuit. In some embodiments, the two-dimensional resonant transducer 25 may be coated with a sensing film 21 applied onto the sensing region between the electrodes. The transducer antenna 27 may be in the form of coiled wire disposed in a plane. The two-dimensional resonant transducer 25 may be wired or wireless. In some embodiments, the two-dimensional resonant transducer 25 may also include an IC chip 29 coupled to transducer antenna 27. The IC chip 29 may store manufacturing, user, calibration and/or other data. The IC chip 29 is an integrated circuit device and it includes RF signal modulation circuitry that may be fabricated using a complementary metal-oxide semiconductor (CMOS) process and a nonvolatile memory. The RF signal modulation circuitry components may include a diode rectifier, a power supply voltage control, a modulator, a demodulator, a clock generator, and other components.

Sensing is performed via monitoring of the changes in the complex impedance spectrum of the two-dimensional resonant transducer 25 as probed by the electromagnetic field 23 generated in the transducer antenna 27. The electromagnetic field 23 generated in the transducer antenna 27 extends out from the plane of the two-dimensional resonant transducer 25 and is affected by the dielectric property of the ambient environment, providing the opportunity for measurements of physical, chemical, and biological parameters.

Figure 5:
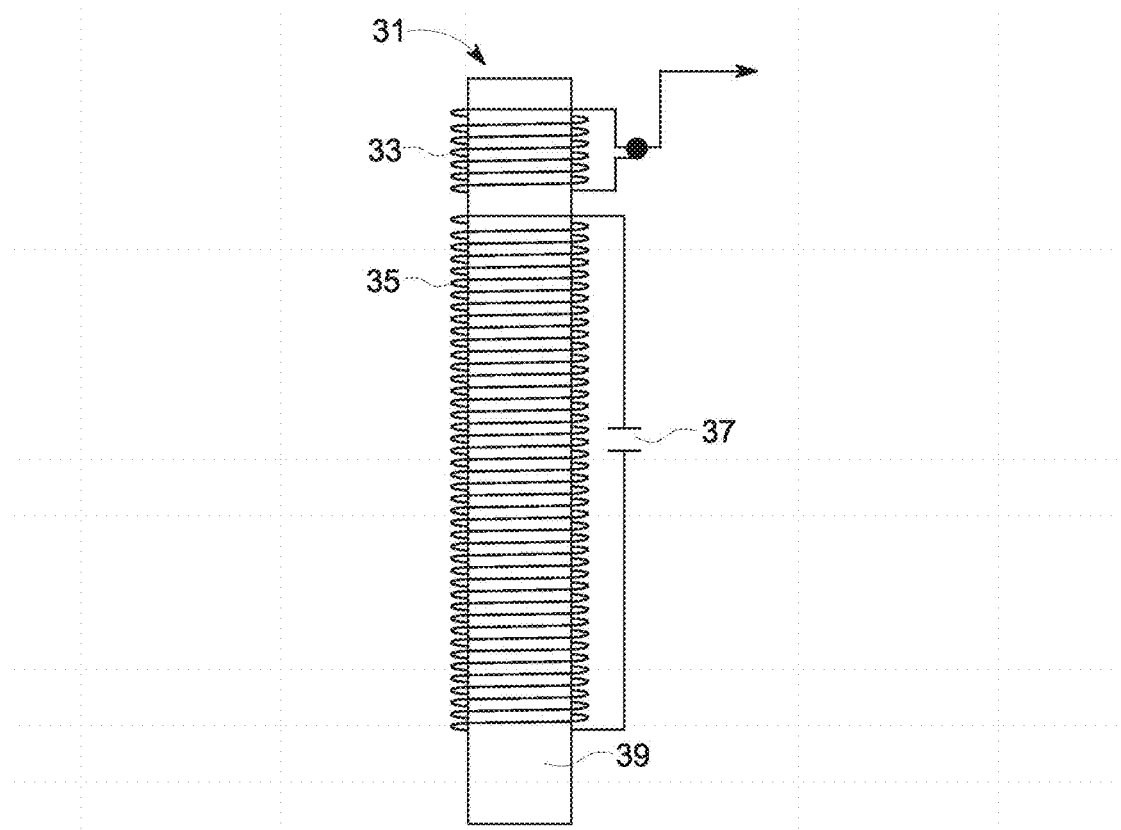
FIG. 5 illustrates an embodiment of a three-dimensional resonant transducer.

Shown in FIG. 5 is a three-dimensional resonant transducer 31. The three-dimensional resonant transducer 31 includes a top winding 33 and a bottom winding 35 coupled to a capacitor 37. The top winding 33 is wrapped around an upper portion of a sampling cell 39 and the bottom winding 35 is wrapped around a lower portion of the sampling cell 39. The sampling cell 39 may, for example, be made of a material resistant to fouling such as Polytetrafluoroethylene (PTFE), a synthetic fluoropolymer of tetrafluoroethylene.

Figure 6:
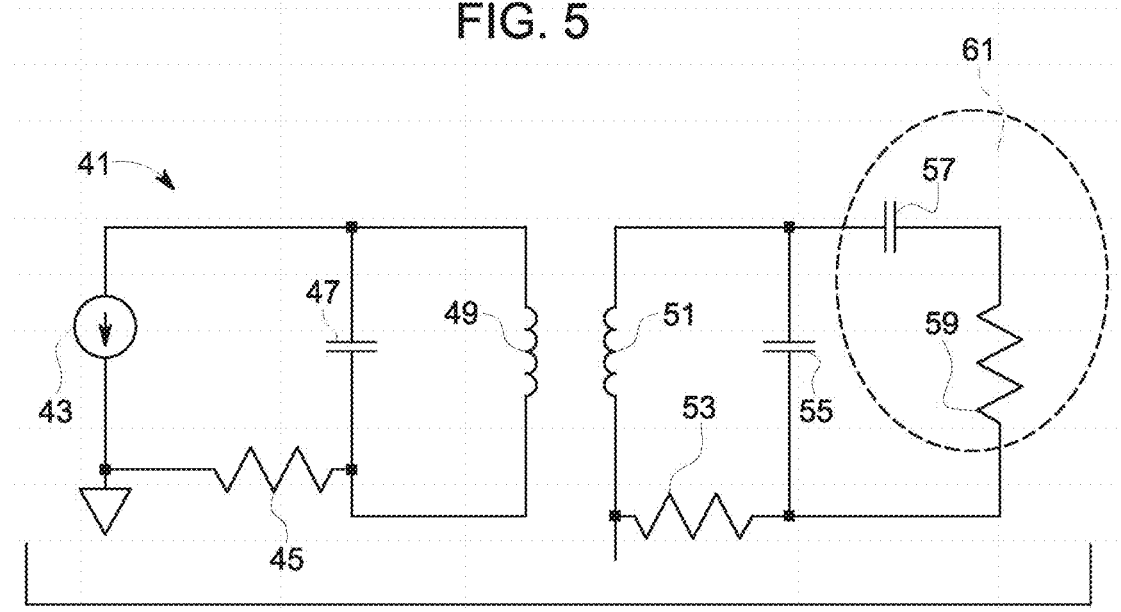
FIG. 6 is a schematic electrical diagram of the equivalent circuit of a three-dimensional resonant transducer.
Figure 7:
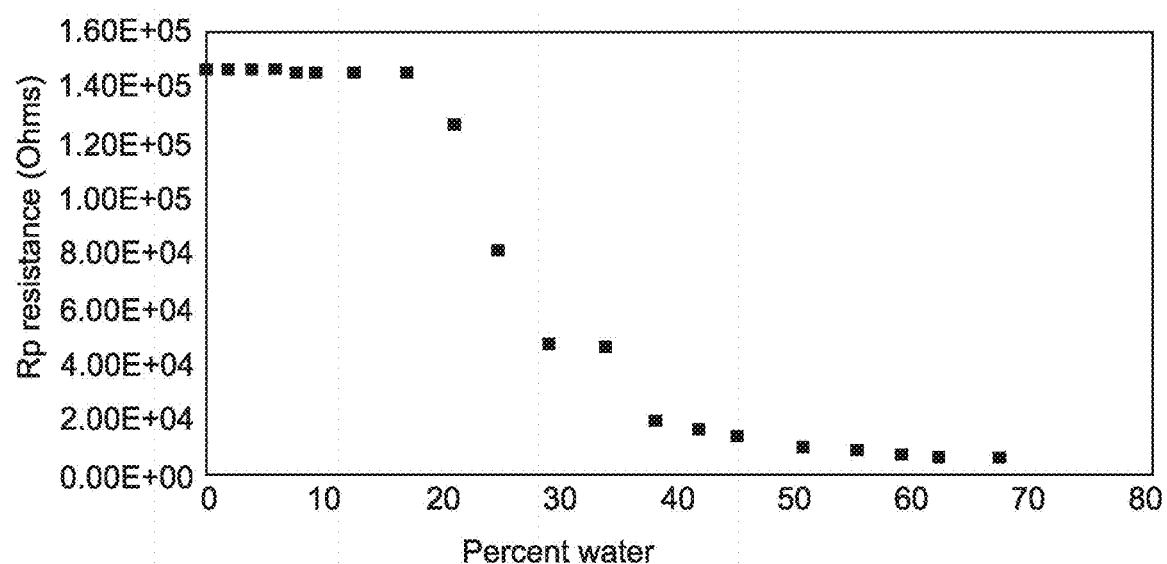
FIG. 7 is a chart illustrating the Rp response of a resonant transducer to varying mixtures of oil and water.
Figure 8:
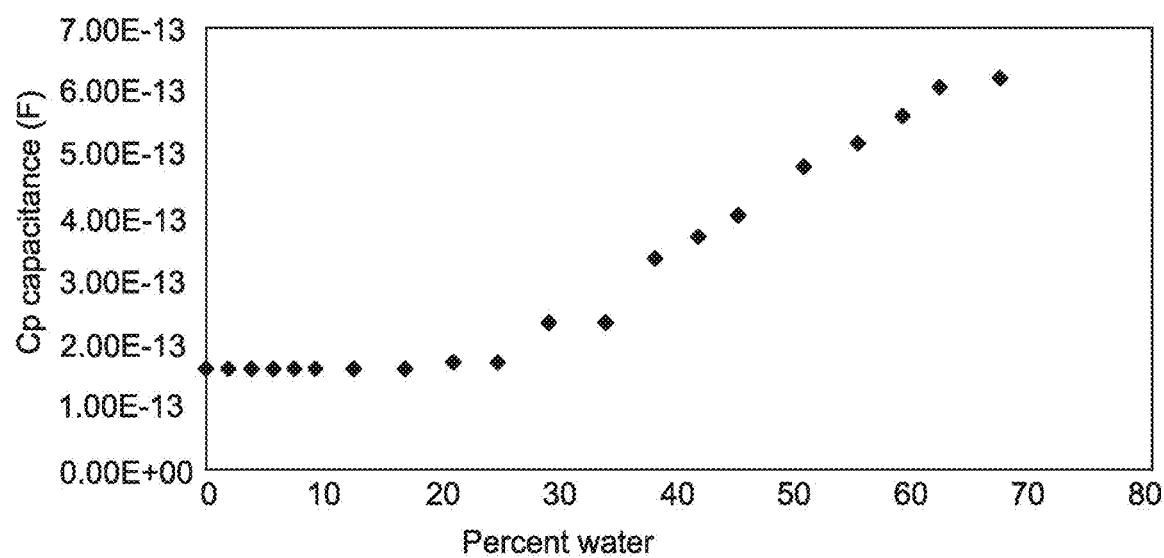
FIG. 8 is a chart illustrating the Cp response of a resonant transducer to varying mixtures of oil and water.

The three-dimensional resonant transducer 31 utilizes mutual inductance of the top winding 33 to sense the bottom winding 35. Illustrated in FIG. 6 is an equivalent circuit 41, including a current source 43, R0 resistor 45, C0 capacitor 47, and L0 inductor 49. The equivalent circuit 41 also includes L1 inductor 51, R1 resistor 53 and C1 capacitor 55. The circuit also includes Cp capacitor 57 and Rp resistor 59. The circled portion of the equivalent circuit 41 shows a sensitive portion 61 that is sensitive to the properties of the surrounding test fluid. A typical Rp response and Cp response of resonant a transducer 12 to varying mixtures of oil and water are shown in FIGS. 7 and 8 respectively.

Figure 9:
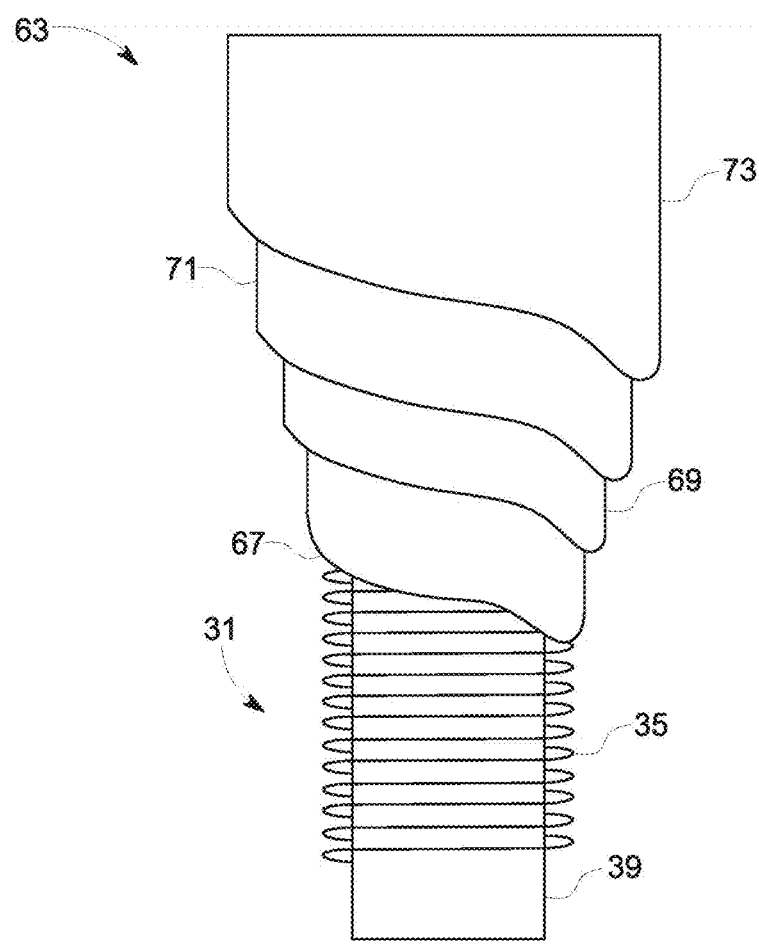
FIG. 9 is a partial cutaway side view of an embodiment of a resonant transducer assembly.

The three-dimensional resonant transducer 31 may be shielded as shown in FIG. 9. A resonant transducer assembly 63 includes a radio frequency absorber (RF absorber layer 67) surrounding the sampling cell 39, top winding 33, and bottom winding 35. A spacer 69 may be provided surrounded by a metal shield 71. The metal shield 71 is optional, and is not part of the transducer 31. The metal shield 71 allows operation inside or near metal objects and piping, reduces noise, and creates a stable environment such that any changes in the sensor response is directly due to changes in the test fluid. In order to successfully encapsulate the sensor in a metal shield 71 the RF absorber layer 67 may be placed between the sensor and the metal shield 71. This prevents the RF field from interacting with the metal and quenching the response of the sensor. The metal shield 71 may be wrapped with a cover 73 of suitable material. The RF absorber layer 67 can absorb electromagnetic radiation in different frequency ranges with non-limiting examples in the kilohertz, megahertz, gigahertz, terahertz frequency ranges depending on the operation frequency of the transducer 31 and the potential sources of interference. The absorber layer 67 can be a combination of individual layers for particular frequency ranges so the combinations of these individual layers provide a broader spectral range of shielding.

Fouling of the resonant sensor system 11 may be reduced by providing the resonant transducer 12 with a geometry that enables resonant transducer 12 to probe the environment over the sample depth perpendicular to the transducer ranging from 0.1 mm to 1000 mm. Signal processing of the complex impedance spectrum reduces the effects of fouling over the sample depth.

Figure 22:
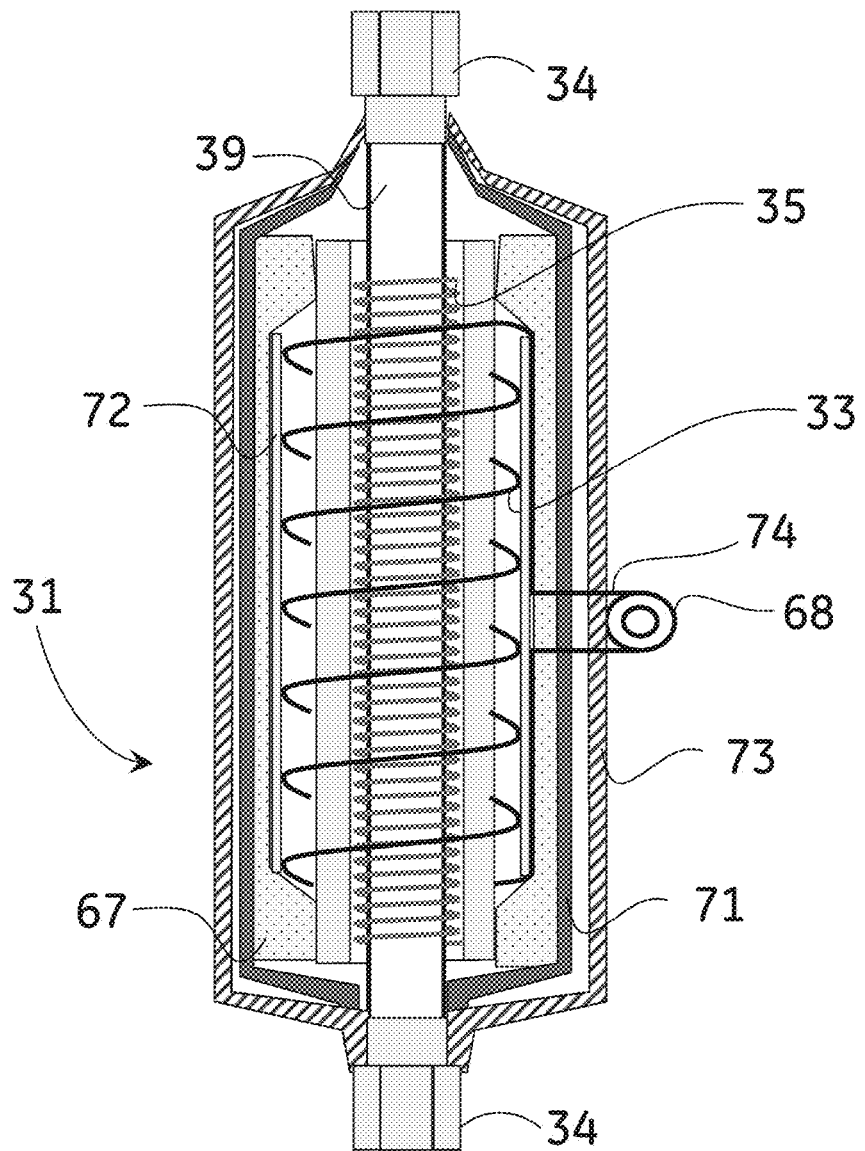
FIG. 22 illustrates another embodiment of a three-dimensional resonant transducer.

Shown in FIG. 22 is a second three-dimensional resonant transducer 31. The second three-dimensional resonant transducer 31 includes a top winding 33 and a bottom winding 35. The bottom winding 35 is located around the sampling cell 39 and the top winding 33 is located around the bottom winding 35. The sampling cell 39 may, for example, be made of a material resistant to fouling and suitable for providing galvanic isolation between the bottom winding 35 and a fluid being sampled such as Polytetrafluoroethylene (PTFE), a synthetic fluoropolymer of tetrafluoroethylene. The sampling cell 39 may be in the form of a tube or otherwise adapted to contain a stationary or flowing fluid, typically a liquid. The fluid may comprise liquid or solid particles mixed with a liquid as in an emulsion, colloidal suspension, latex or other dispersion. A galvanic isolator 34 is preferably provided between the top winding 33 and the bottom winding 35 although the top winding 33 and bottom winding 35 might also be separated by an air gap. For example, the galvanic isolator 34 may be a PTFE tube. The bottom winding 35 may be wound directly around a portion of the sampling cell 39 or otherwise fit around, or be in contact with, the outside of the sampling cell 39. The top winding 33 may be separated from the bottom winding 35 by a spacing of about 0.1" to 0.3" (2.5 to 7.5 mm). The top winding 33 and the bottom winding 35 are preferably arranged as tubular coils concentric with each other and the sampling cell 39.

The second three-dimensional resonant transducer 31 has a spacer 72 between the top winding 33 and the RF absorber layer 67. The spacer 72 is made of galvanic isolating material. This spacer 72 increases signal while reducing noise resulting in a higher signal to noise ratio. The inventors have also observed that this spacer 72 can enhance the dynamic range of the second three-dimensional resonant transducer 31.

The second three-dimensional resonant transducer 31 has wires 74 connecting the ends of the top winding 33 to a connector 68. The connector 68 is used to connect an electrical cable from the analyzer 15 to the second three-dimensional resonant transducer 31. The second three-dimensional resonant transducer 31 also has fittings 34 at the ends of the sampling cell 39. The fittings 34 allow the sampling cell 39 to be optionally connected to one or more pipes, which may have valves or other flow control devices, adapted to bring a liquid sample into the sampling cell 39 and to remove a sample after it has been measured.

Optionally, the second three-dimensional resonant transducer 31 may have two galvanically isolated top windings 33, one that is used as a drive (excitation) coil and one that is used as a pick up (receiving) coil. However, in the example of FIG. 22, a single top winding 33 acts as both a drive coil and a pick up coil. Analyzer 15 is configured to both send current (typically a sinusoidal power wave) through the top winding 33 and to receive a signal (current) from the top winding but at different time intervals, for example according to an alternating pattern of excitation and receiving. The excitation and receiving steps may each have a duration of, for example, 0.2 to 5 seconds. The frequency of the power wave applied during the excitation stage may vary between successive excitation stages. In addition to avoiding a second top winding 33, this configuration avoids having two sets of electrical cables connecting the analyzer 15 to the second three-dimensional resonant transducer 31 and this tends to reduce signal noise.

The bottom winding 35 acts as a resonator or sensing coil. The bottom winding 35 floats with no galvanic connections to other parts of the second three-dimensional resonant transducer 31. The two ends of the bottom winding 35 are preferably not connected to each other (other than through the coils of the bottom winding 35) so as to form a circuit loop, although connections to form a circuit as in FIG. 5, with or without a capacitor, may also be used. The bottom winding 35 is excited by an electro-magnetic field created by a power wave flowing through the top winding 33. The excited bottom winding 35 generates another electro-magnetic field that is altered by its interaction with the fluid in the sampling cell 39. This (refelected) electro-magnetic field is then and sensed by the top winding 33. As mentioned above, these two steps occur in different time periods, preferably repeated in alternation over a plurality of cycles.

Although the bottom winding 35 generates an electromagnetic field, because the sampling cell 39 contains a fluid (such as water or oil) with low conductivity, signals representing the electric (as opposed to magnetic) portion of the field generated by the bottom winding 35 are the primary or only means of analysis. This is in contrast to eddy current techniques used when making measurements of more conductive materials that use the magnetic portion of a field generated by a resonator as the primary or only means of analysis. Signals associated with the magnetic portion of the electro-magenetic field generated by the bottom winding 35 would tend to indicate the conductivity of a sample whereas signals associated with the electric portion of the electromagenetic field generated by the bottom winding 35 indicate the impedance of the sample.

The analyzer 15 translates the electric response (signal) generated by the bottom winding 33 (as received through the top winding 35) into one or more measured parameters. These parameters may include one or more of: complex (magnitude and phase) impedance response; resonance peak position, peak width, peak height and/or peak symmetry of the impedance response; magnitude of the real part of the impedance; resonant frequency of the imaginary part of the impedance; antiresonant frequency of the imaginary part of the impedance; zero-reactnace frequency; phase angle of impedance; magnitude of impedance; and, others.

The second three-dimensional resonant transducer 31 of FIG. 22 may be used in any method or apparatus described for the resonant transducer 31 of FIG. 5. The second three-dimensional resonant transducer 31 of FIG. 22 utilizes mutual inductance of the top winding 33 to sense the bottom winding 35. The equivalent circuit in FIG. 6 may be used with the second three-dimensional resonant transducer 31 of FIG. 22. An Rp response and Cp response to varying mixtures of oil and water similar to that shown in FIGS. 7 and 8 respectively may be obtained from the second three-dimensional resonant transducer 31 of FIG. 22.

The second three-dimensional resonant transducer 31 may be shielded as shown in FIG. 22. A resonant transducer assembly 63 includes a radio frequency absorber (RF absorber layer 67) surrounding the sampling cell 39, top winding 33, and bottom winding 35. The RF absorber layer 67 may be surrounded by a metal, for example aluminum, shield 71. There may be a spacer (not shown) between the RF absorber layer 67 and the shield 71. The shield 71 is optional, and is not a necessary part of the second three-dimensional resonant transducer 31. However, the shield 71 improves operation inside or near metal objects and piping, reduces noise, and creates a stable environment such that any changes in the sensor response is directly due to changes in the test fluid. In order to successfully encapsulate the sensor in a shield 71 the RF absorber layer 67 may be placed between the sensor and the metal shield 71. This prevents the RF field from interacting with the metal and quenching the response of the sensor. The metal shield 71 may be wrapped with a cover 73 of suitable material. The RF absorber layer 67 can absorb electromagnetic radiation in different frequency ranges with non-limiting examples in the kilohertz, megahertz, gigahertz, terahertz frequency ranges depending on the operation frequency of the transducer 31 and the potential sources of interference. The absorber layer 67 can be a combination of individual layers for particular frequency ranges so the combinations of these individual layers provide a broader spectral range of shielding.

The top winding 33 is preferably, but not necessarily, at least half as long as the bottom winding 35. The top winding 33 preferably, but not necessarily, has a larger pitch than the bottom winding 35. For example, as shown in in FIG. 22, the top winding 33 is about as long as the bottom winding 35 but has less than one tenth as many turns as the bottom winding 35. For example, the top winding 33 may have one turn for every 15 to 50 turns of the bottom winding 35. The top winding 33 and the bottom winding 35 have different resonant frequencies. When measuring the concentration of water in oil or oil in water, or the concentration of salts or solid particles in a water, or oil, or water and oil, based mixture, the top winding 33 preferably has a higher resonant frequency than the bottom winding 35. The resonant frequencies of the top winding 33 and the bottom winding 35 are preferably baseline separated. Successive peaks of the applied and reflected (modified by interaction with the sample) signals are separated by at least some distance along the baseline.

The concentric arrangement of the top winding 33 and the bottom winding 35 shown in FIG. 22 increases the sensitivity of the second three-dimensional resonant transducer 31. For example, the second three-dimensional resonant transducer 31 of FIG. 22 may be better able to determine the composition of emulsions and other dispersions, including dispersions of solid particles and dispersions containing both solid particles and an emulsion, compared to the resonant transducer 31 of FIG. 5. However, the resonant transducer of FIG. 5 may also be used to determine the composition of emulsions and other dispersions, including dispersions of solid particles and dispersion containing both solid particles and an emulsion.

Figure 10:
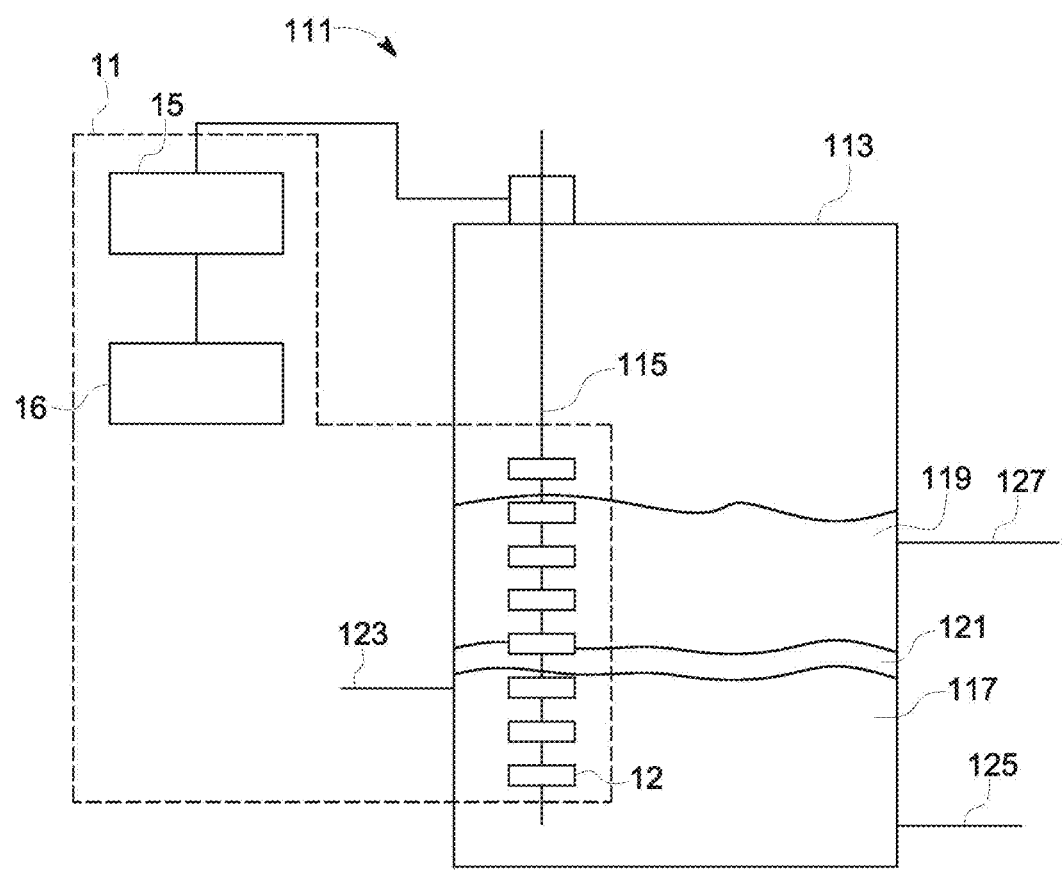
FIG. 10 is a schematic diagram of an embodiment of a fluid processing system.

As shown in FIG. 10, the resonant sensor system 11 may be used to determine the level and composition of fluids in a fluid processing system 111. Fluid processing system 111 includes a vessel 113 with a sampling assembly 115 and a resonant sensor system 11. The resonant sensor system 11 includes at least one resonant transducer 12 coupled to the sampling assembly 115. Resonant sensor system 11 also includes an analyzer 15 and a processor 16.

In operation, a normally immiscible combination of fluids enters the vessel through a raw fluid input 123. The combination of fluids may include a first fluid and a second fluid normally immiscible with the first fluid. As the combination of fluids is processed, the combination of fluids is separated into a first fluid layer 117, and a second fluid layer 119. In between the first fluid layer 117 and second fluid layer 119, there may be a rag layer 121. After processing, a first fluid may be extracted through first fluid output 125, and a second fluid may be extracted through second fluid output 127. The resonant sensor system 11 is used to measure the level of the first fluid layer 117, the second fluid layer 119 and the rag layer 121. The resonant sensor system 11 may also be used to characterize the content of the first fluid layer 117, the second fluid layer 119 and the rag layer 121.

Figure 11:
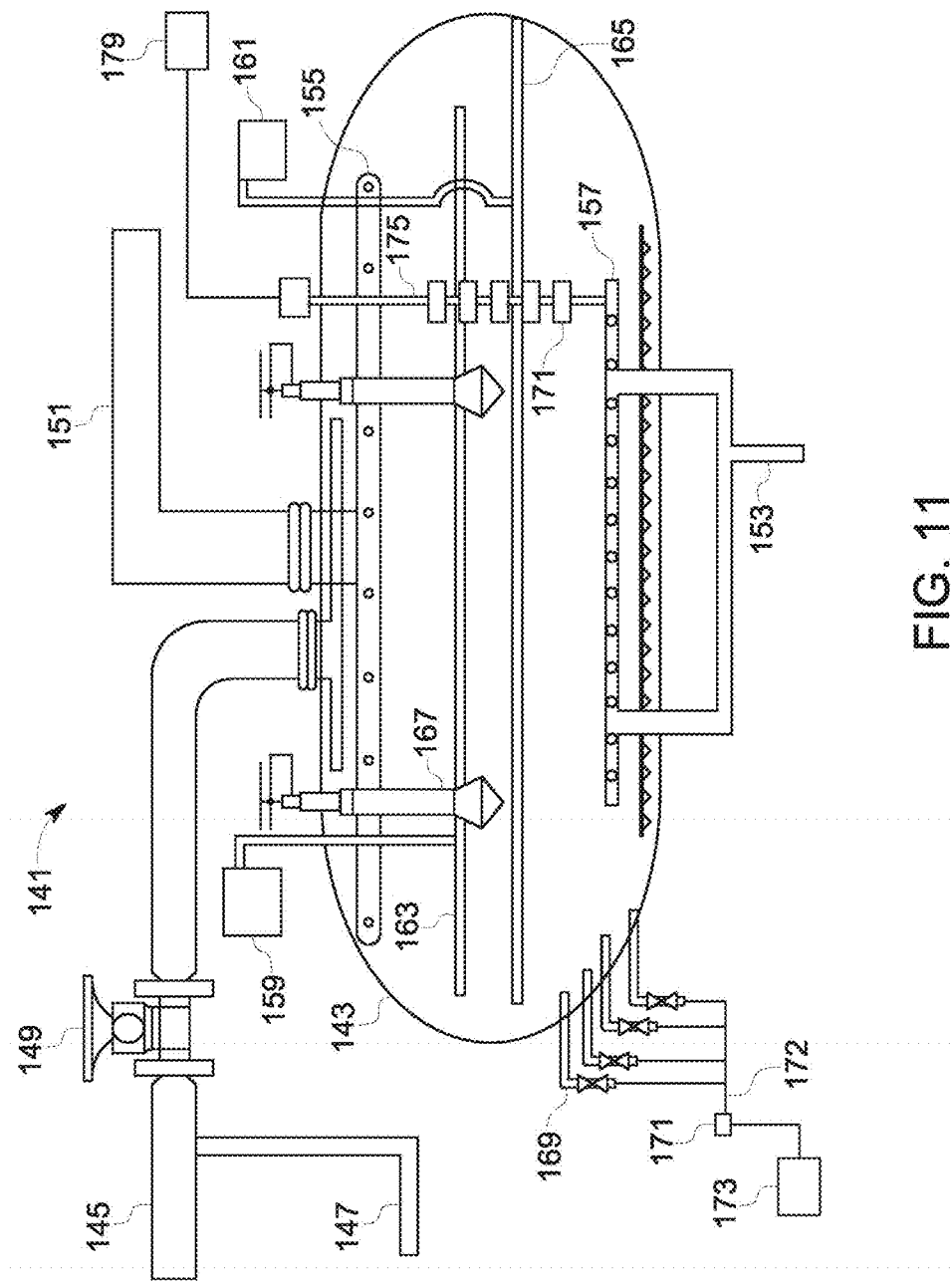
FIG. 11 is a schematic diagram of an embodiment of a desalter.

An embodiment of a fluid processing system 111 is a desalter 141 illustrated in FIG. 11. The desalter 141 includes a desalter vessel 143. Raw oil enters the desalter 141 through crude oil input 145 and is mixed with water from water input 147. The combination of crude oil and water flows through mixing valve 149 and into the desalter vessel 143. The desalter 141 includes a treated oil output 151 and a wastewater output 153. Disposed within the desalter vessel 143 are an oil collection header 155 and a water collection header 157. Transformer 159 and transformer 161 provide electricity to top electrical grid 163 and bottom electrical grid 165. Disposed between top electrical grid 163 and bottom electrical grid 165 are emulsion distributors 167.

In operation, crude oil mixed with water enters the desalter vessel 143 and the two fluids are mixed and distributed by emulsion distributors 167 thereby forming an emulsion. The emulsion is maintained between the top electrical grid 163 and the bottom electrical grid 165. Salt containing water is separated from the oil/water mixture by the passage through the top electrical grid 163 and bottom electrical grid 165 and drops towards the bottom of the desalter vessel 143 where it is collected as waste water.

Control of the level of the emulsion layer and characterization of the contents of the oil-in-water and water-in-oil emulsions is important in the operation of the desalter 141. Determination of the level of the emulsion layer may be accomplished using a sampling assembly such as a try-line assembly 169 coupled to the desalter vessel 143 and having at least one resonant transducer 12 disposed on try-line output conduit 172. The resonant transducer 12 may be coupled to a data collection component 173. In operation, the resonant transducer 12 is used to measure the level of water and the oil and to enable operators to control the process. The try-line assembly 169 may be a plurality of pipes open at one end inside the desalter vessel 143 with an open end permanently positioned at the desired vertical position or level in the desalter vessel 143 for withdrawing liquid samples at that level. There are generally a plurality of sample pipes in a processing vessel, each with its own sample valve, with the open end of each pipe at a different vertical position inside the unit, so that liquid samples can be withdrawn from a plurality of fixed vertical positions in the unit. Another approach to measuring the level of the emulsion layer is to use a swing arm sampler. A swing arm sampler is a pipe with an open end inside the desalter vessel 143 typically connected to a sampling valve outside the unit. It includes an assembly used to change the vertical position of the open end of the angled pipe in the desalter 141, by rotating it, so that liquid samples can be withdrawn (or sampled) from any desired vertical position.

Another method to measure the level of the oil and water is to dispose at least one resonant transducer 12 on a dipstick 175. A dipstick 175 may be a rod with a resonant transducer 12 that is inserted into the desalter vessel 143. Measurements are made at a number of levels. Alternately, the dipstick 175 may be a stationary rod having a plurality of multiplexed resonant transducers 12. The resonant transducer 12 may be coupled to a data collection component 179 that collects data from the various readings for further processing.

Figure 12:
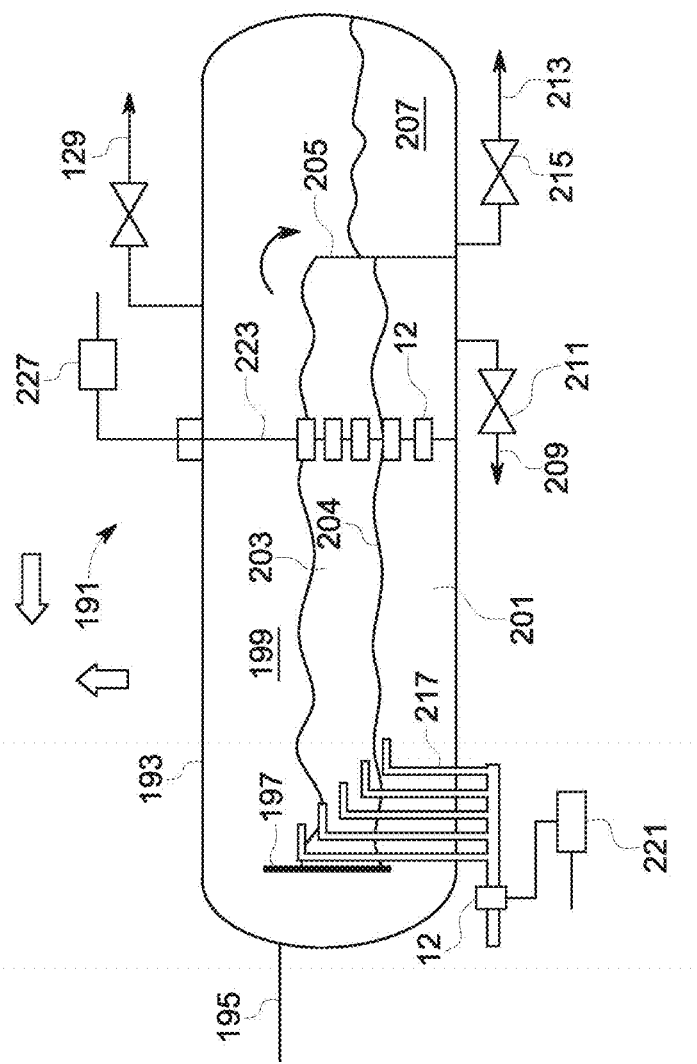
FIG. 12 is a schematic diagram of an embodiment of a separator.

Another embodiment of a fluid processing system 111 is a separator 191 illustrated in FIG. 12. The separator 191 includes a separator vessel 193 having an input conduit 195 for crude oil. Crude oil flowing from input conduit 195 impacts an inlet diverter 197. The impact of the crude oil on the inlet diverter 197 causes water particles to begin to separate from the crude oil. The crude oil flows into the processing chamber 199 where it is separated into a water layer 201 and an oil layer 203. The crude oil is conveyed into the processing chamber 199 below the oil/water interface 204. This forces the inlet mixture of oil and water to mix with the water continuous phase in the bottom of the vessel and rise through the oil/water interface 204 thereby promoting the precipitation of water droplets which are entrained in the oil. Water settles to the bottom while the oil rises to the top. The oil is skimmed over a weir 205 where it is collected in oil chamber 207. Water may be withdrawn from the system through a water output conduit 209 that is controlled by a water level control valve 211. Similarly oil may be withdrawn from the system through an oil output conduit 213 controlled by an oil level control valve 215. The height of the oil/water interface may be detected using a try-line assembly 217 having at least one resonant transducer 12 disposed in a try-line output conduit 218 and coupled to a data processor 221. Alternately a dip stick 223 having at least one resonant transducer 12 coupled to a processor 227 may be used to determine the level of the oil/water interface 204. The determined level is used to control the water level control valve 211 to allow water to be withdrawn so that the oil/water interface is maintained at the desired height.

The following examples are given by way of illustration only and are not intended as a limitation of the scope of this disclosure. A model system of heavy mineral oil, tap water and detergent was used to carry out static tests for various designs of resonant transducer 12. The level of detergent was kept constant for all of the mixtures.

Example 1

Figure 13:
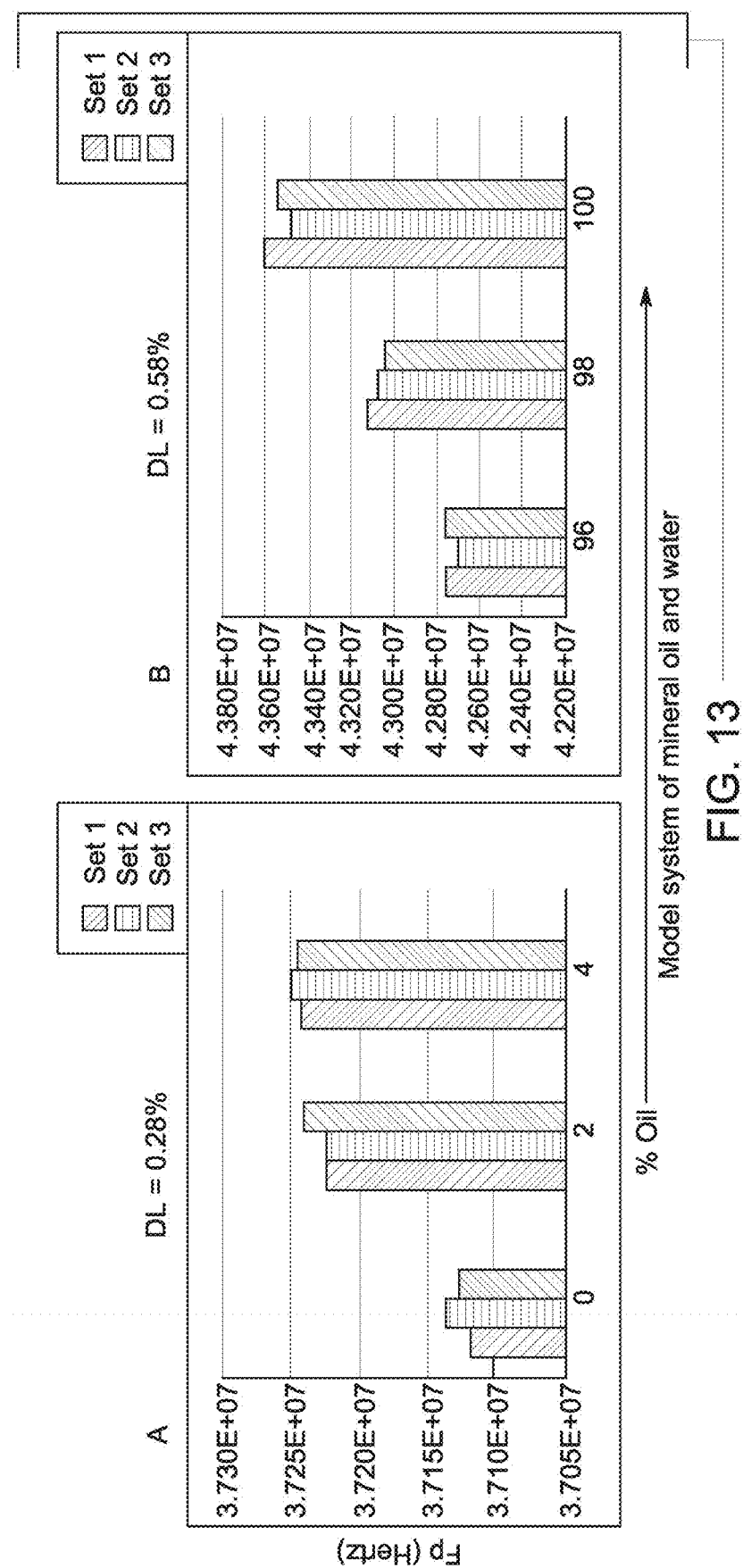
FIG. 13 is a chart illustrating the frequency (Fp) response of a three-dimensional resonant transducer to increasing concentrations of oil-in-water and water-in-oil emulsions.

In the case of the three-dimensional resonant transducer 31 disposed on a try-line or swing arm sampling assembly 13, different compositions of oil and water were poured into a sample cell with the three-dimensional resonant transducer 31 wound around the outside of the sample cell. FIG. 13 shows the try-line/swing arm response in terms of Fp (frequency shift of the real impedance) as oil concentration increases. The calculated detection limit of the composition of oil in oil-in-water emulsions (FIG. 13 part A) is 0.28% and of oil in water-in-oil emulsions (FIG. 13 part B) is 0.58%.

Example 2

Figure 14:
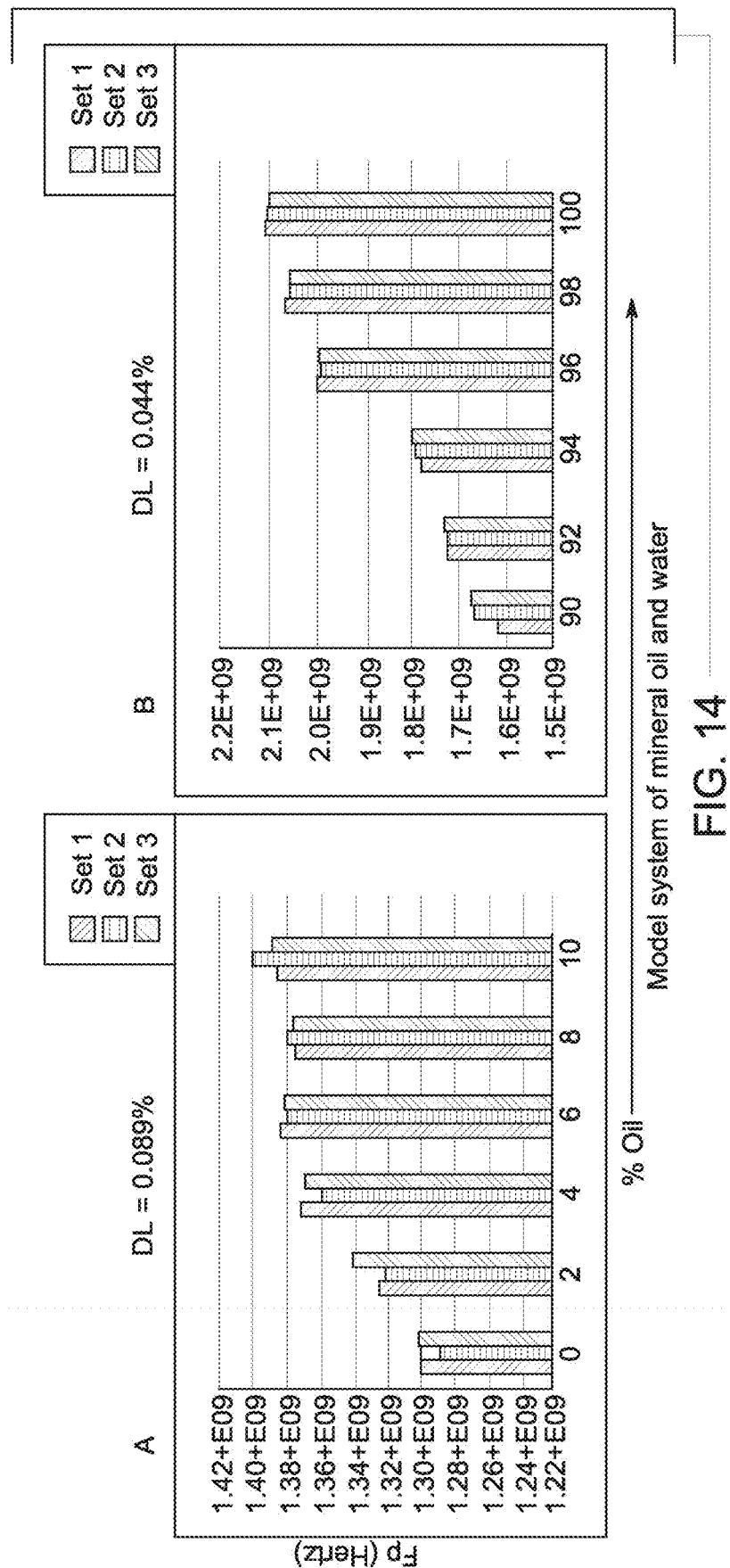
FIG. 14 is a chart illustrating the frequency (Fp) response of a two-dimensional resonant transducer to increasing concentrations of oil-in-water and water-in-oil emulsions.

In the case of the two-dimensional resonant transducer 25, the two-dimensional resonant transducer 25 was immersed in different compositions of oil and water. FIG. 14 shows the response of a two-dimensional resonant transducer 25 (2 cm circular) in terms of Fp (frequency shift of the real impedance) as oil concentration increases. The calculated detection limit of the composition of oil in oil-in-water emulsions (FIG. 14 part A) is 0.089% and of oil in water-in-oil emulsions (FIG. 14 part B) is 0.044%. This example illustrates that small concentrations of one fluid mixed large concentrations of another fluid can be measured with a high degree of accuracy.

Example 3

The model system was loaded with 250 mL of mineral oil and treated with detergent at a concentration of 1 drop per 50 mL (5 drops). The mineral oil was stirred and injected through the sensor and the impedance spectra are recorded. Small additions of water were added with constant salinity and same detergent treatment. After the water volume exceeded 66% or 500 mL of water, the system was cleaned and the experiment is repeated with different salinity waters. The multivariate response of the two-dimensional resonant transducer 25 was sensitive to changes in composition and conductivity at all levels in the test vessel of the model system. Although the effect of conductivity and composition are somewhat convoluted, the fact that the sensor monitors a composition gradient allows the data analysis procedure to deconvolute these effects.

Figure 15:
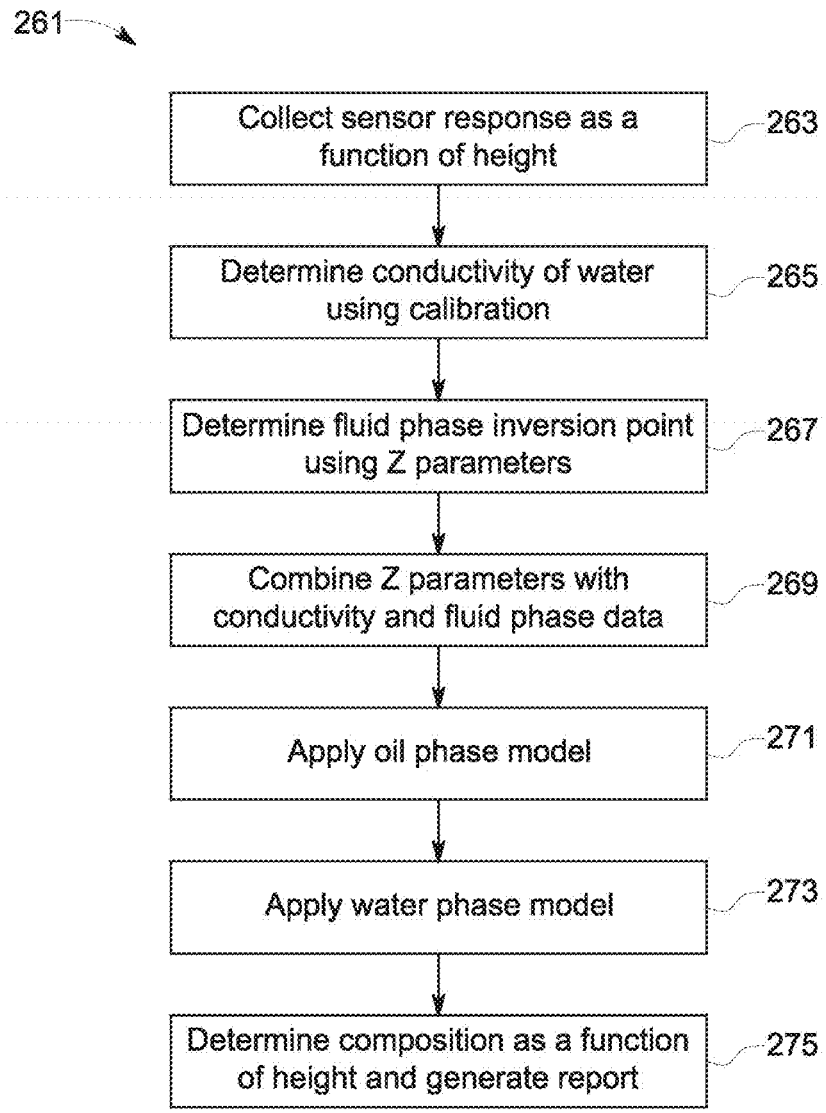
FIG. 15 is a flow chart of an embodiment of a method for determining the composition of an oil and water mixture as a function of height.

FIG. 15 is a generalized process diagram illustrating a method 261 for determining the composition of an oil and water mixture as a function of height.

In step 263 data (a set of LCR resonant circuit parameters) is collected as a function of height from top to bottom (in the lab, this is simulated by starting with 100% oil and gradually adding water).

In step 265 the conductivity of water using calibration is determined. At 100% water, the multivariate response is compared to a calibration for water conductivity.

In step 267 the fluid phase inversion point is determined using Z parameters.

In step 269 the Z parameters are combined with conductivity and fluid phase data.

In step 271 an oil phase model is applied. The oil phase model is a set of values correlating measured frequency values, impedance values and conductivity values to oil content in an oil and water mixture.

In step 273 a water phase model is applied. The water phase model is a set of values correlating measured frequency values, impedance values and conductivity values to water content in a water and oil mixture.

In step 275 the composition as a function of height is determined using the conductivity and the fluid phase inversion point as input parameters in the multivariate analysis and a report is generated.

Figure 16:
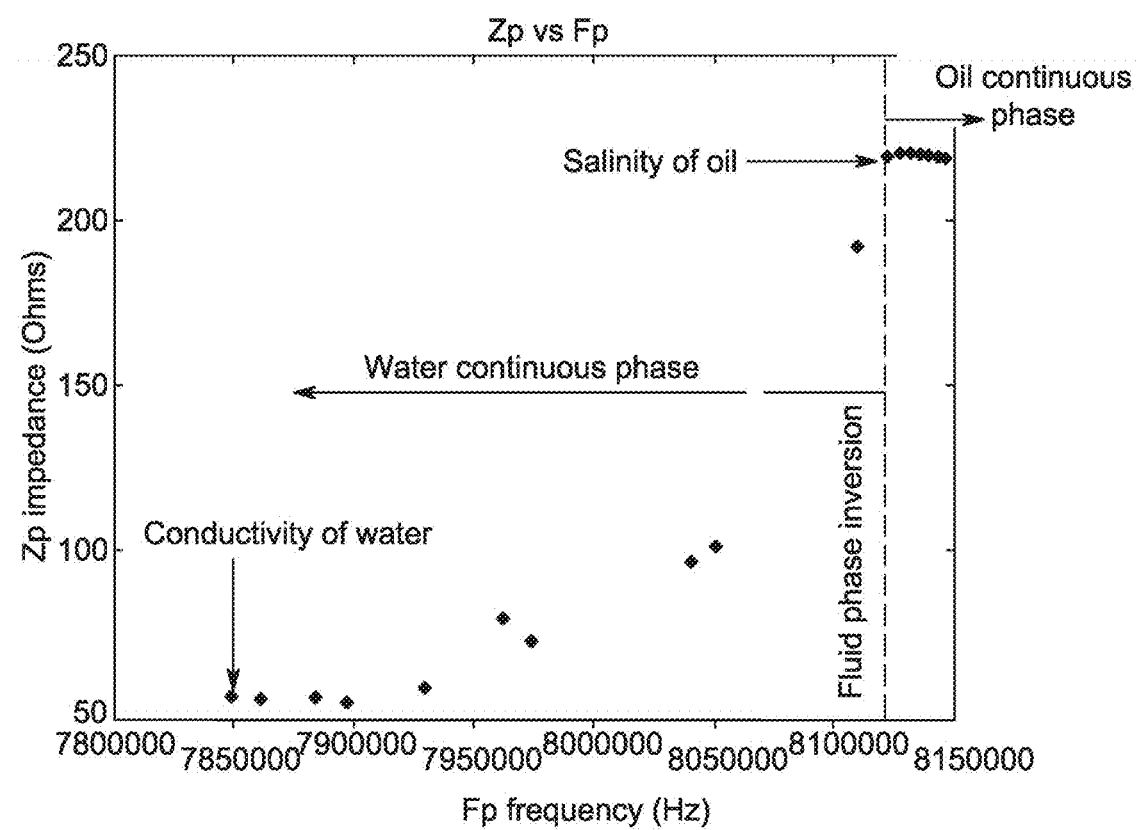
FIG. 16 is a chart illustrating data used to determine a fluid phase inversion point and conductivity.

FIG. 16 shows the raw impedance (Zp) vs. frequency (Fp) data for a profile containing 0-66% water from right to left. At approximately 8.12 MHz, the water content is high enough (~25%) to induce fluid phase inversion from oil to water continuous phase. This is apparent from the drastic change in Zp due to the increased conductivity of the test fluid in water continuous phase. An oil continuous phase model is applied to any data points to the right of the fluid phase inversion and a water model to the left. Additionally, a calibration is applied to the endpoint to determine the conductivity of the water, which in this case was 2.78 mS/cm.

Figure 17:
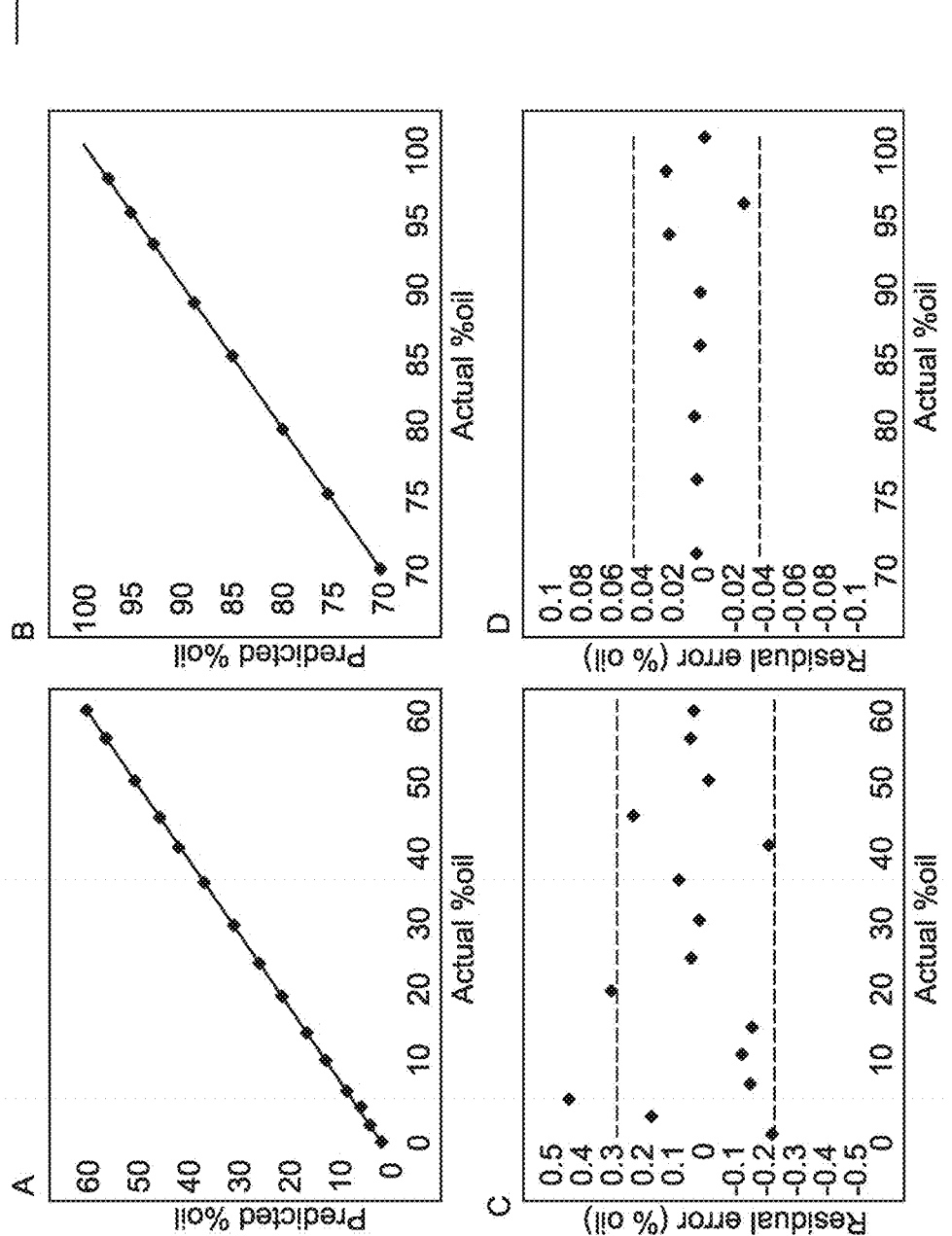
FIG. 17 is a chart illustrating the results of an analysis of the experimental data of an embodiment of a resonant sensor system.

FIG. 17 shows the results of an analysis of the experiment data from an embodiment of a three-dimensional resonant sensor system illustrated the correlation between the actual and predicted values of oil in water and water in oil and the residual errors of prediction based on developed model. Part A of the chart plots the actual and predicted values of oil in water. Part B of the chart plots the actual and predicted values of water in oil. In part A, the data points were modeled separately from the data points in part B (water continuous phase). Parts C and D of the chart plot the residual error between the actual and predicted values of oil in water and water in oil respectively. Generally, the residual error was less than 0.5% when the actual percentage of oil is between 0% to 60%. The residual error was less than 0.04% when the actual percentage of oil is between 70% to 100%. At the fluid phase inversion the residual error increases up to 10% where prediction capability is difficult due to fluctuations in the composition of the test fluid in the dynamic test rig. The prediction capability of the sensor will improve at compositions >66% water with more training data.

Figure 18:
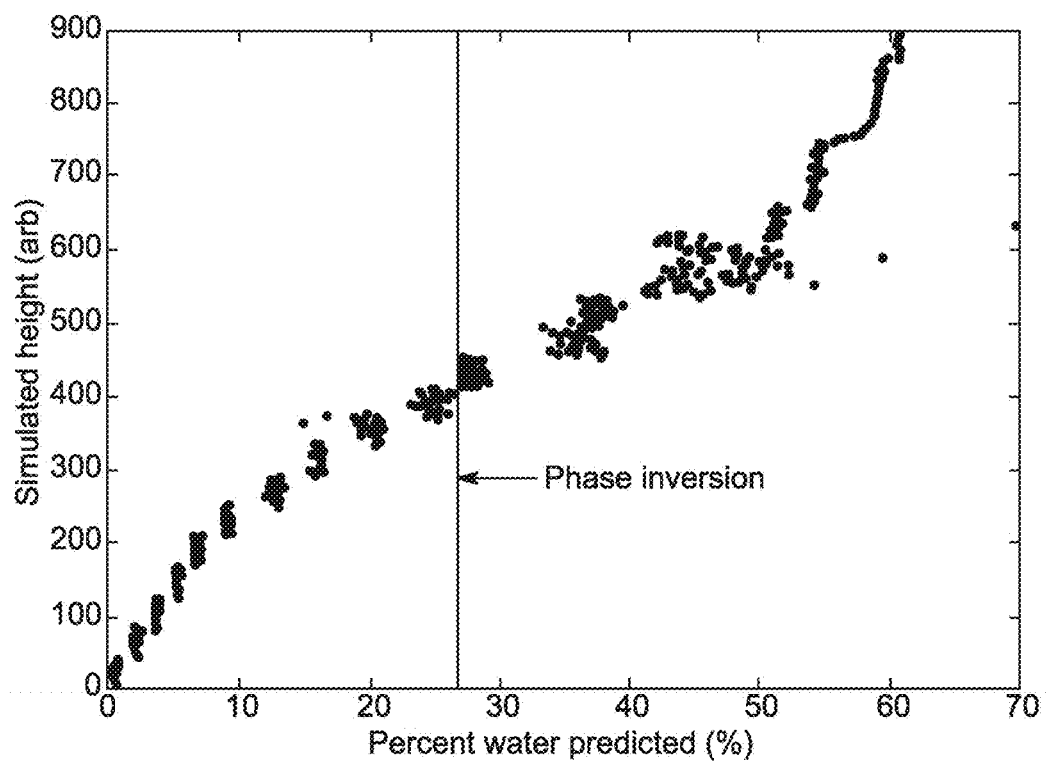
FIG. 18 is a chart illustrating test results of a resonant sensor system in a simulated desalter.

FIG. 18 illustrates the results obtained in a simulated desalter. The chart shows a profile developed by plotting the composition as a function of time. To simulate the sampling using a swing arm that is slowly rotated through the rag layer, a test rig was operated such that the composition of the test fluid was slowly modulated with time by adding small additions of water.

Figure 19:
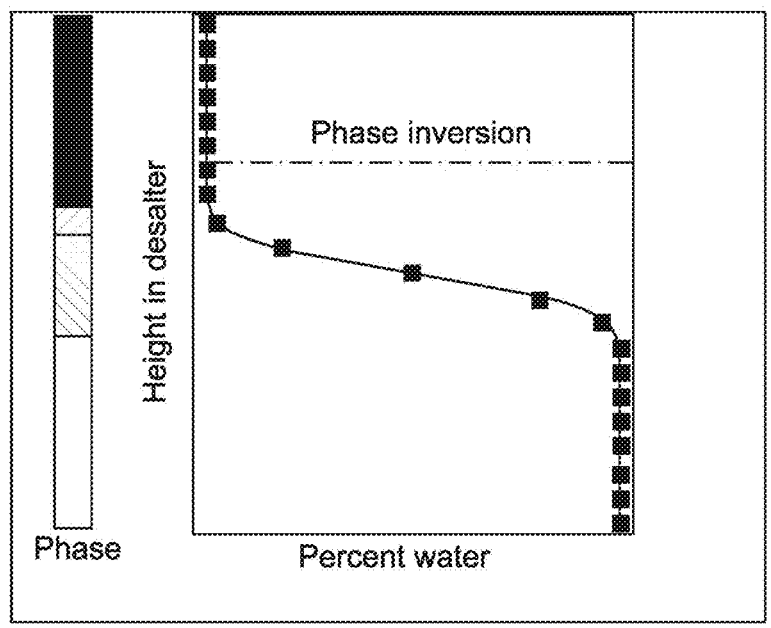
FIG. 19 is an embodiment of a display of a data report from a resonant sensor system.

FIG. 19 is an illustration of the expected level of reporting from the sensor data analysis system. The end user will be shown a plot that displays a representation of the composition as a function of height in the desalter, the level of fluid phase inversion, and the width of the rag layer. On the left are fluid phase indicators (black-oil, gray-oil continuous, cross hatched-water continuous, white-water) that indicate the percent water/height curve. The height of the rag layer is the sum of the water continuous and oil continuous regions. The level of detail indicated will allow the operator of the desalter to optimize the feed rate of chemicals into the process, provide more detailed feedback on the performance of a fluid processing system, and highlight process upsets that may cause damage to downstream process infrastructure.

Figure 20:
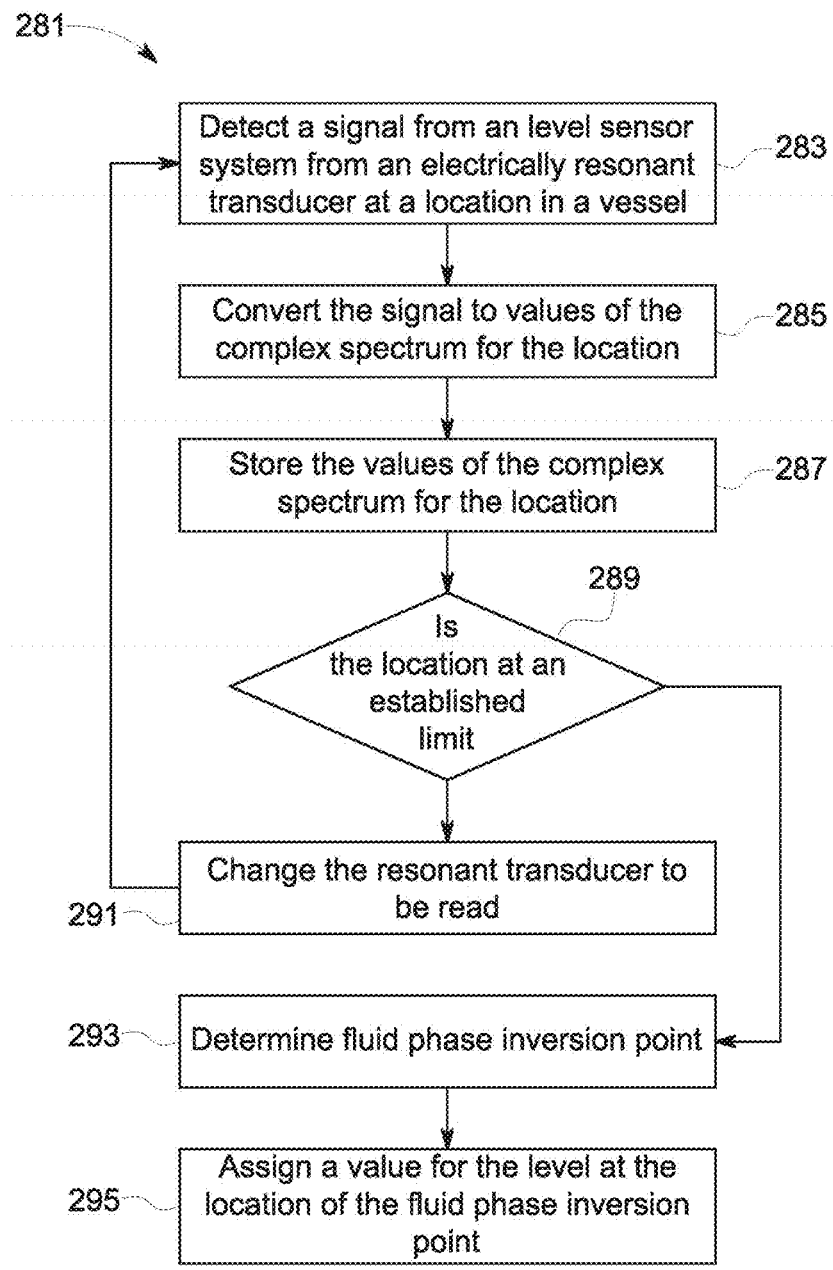
FIG. 20 is a flowchart of an embodiment of a method for determining the level of a fluid in a vessel.

Illustrated in FIG. 20 is a method 281 for measuring the level of a mixture of fluids in a vessel 113.

In step 283, the method 281 may detect signals (a set of signals) from a resonant sensor system 11 at a plurality of locations in a vessel. The signals are generated by a resonant transducer 12 immersed in the mixture of fluids. The resonant transducer 12 generates a set of transducer signals corresponding to changes in dielectric properties of the resonant transducer 12, and the signals are detected by an analyzer 15.

In step 285, the method 281 may convert the signals to a set of values of the complex impedance spectrum for the plurality of locations. The conversion is accomplished using multivariate data analysis.

In step 287, the method 281 may store the values of the complex impedance spectrum.

In step 289, the method 281 may determine if a sufficient number of locations have been measured.

In step 291, the method 281 may change the resonant transducer 12 being read (or the location of the resonant transducer 12) if an insufficient number of locations have been measured.

In step 293, the method 281 may determine the fluid phase inversion point if a sufficient number of locations has been measured. The fluid phase inversion point is determined from the values of the complex impedance spectrum by identifying a drastic change in the impedance values.

In step 295, the method 281 may assign a value for the interface level based on the fluid phase inversion point.

Figure 21:
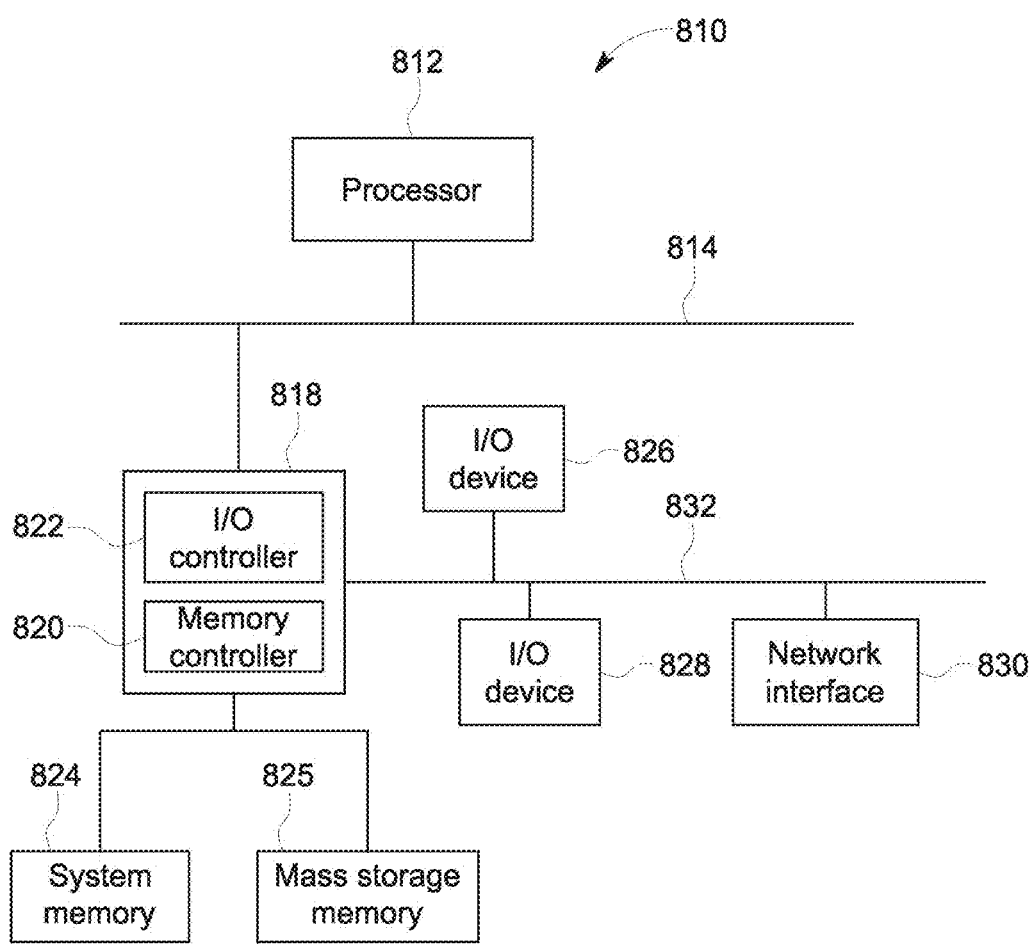
FIG. 21 is a block diagram of a non-limiting representative embodiment of a processor system for use in a resonant sensor system.

FIG. 21 is a block diagram of non-limiting example of a processor system 810 that may be used to implement the apparatus and methods described herein. As shown in FIG. 21, the processor system 810 includes a processor 812 that is coupled to an interconnection bus 814. The processor 812 may be any suitable processor, processing unit or microprocessor. Although not shown in FIG. 21, the processor system 810 may be a multi-processor system and, thus, may include one or more additional processors that are identical or similar to the processor 812 and that are communicatively coupled to the interconnection bus 814.

The processor 812 of FIG. 21 is coupled to a chipset 818, which includes a memory controller 820 and an input/output (I/O) controller 822. As is well known, a chipset typically provides I/O and memory management functions as well as a plurality of general purpose and/or special purpose registers, timers, etc. that are accessible or used by one or more processors coupled to the chipset 818. The memory controller 820 performs functions that enable the processor 812 (or processors if there are multiple processors) to access a system memory 824 and a mass storage memory 825.

The system memory 824 may include any desired type of volatile and/or nonvolatile memory such as, for example, static random access memory (SRAM), dynamic random access memory (DRAM), flash memory, read-only memory (ROM), etc. The mass storage memory 825 may include any desired type of mass storage device including hard disk drives, optical drives, tape storage devices, etc.

The I/O controller 822 performs functions that enable the processor 812 to communicate with peripheral input/output (I/O) devices 826 and 828 and a network interface 830 via an I/O bus 832. The I/O devices 826 and 828 may be any desired type of I/O device such as, for example, a keyboard, a video display or monitor, a mouse, etc. The network interface 830 may be, for example, an Ethernet device, an asynchronous transfer mode (ATM) device, an 802.11 device, a DSL modem, a cable modem, a cellular modem, etc. that enables the processor system 810 to communicate with another processor system. Data from analyzer 15 may be communicated to the processor 812 through the I/O bus 832 using the appropriate bus connectors.

While the memory controller 820 and the I/O controller 822 are depicted in FIG. 21 as separate blocks within the chipset 818, the functions performed by these blocks may be integrated within a single semiconductor circuit or may be implemented using two or more separate integrated circuits.

Certain embodiments contemplate methods, systems and computer program products on any machine-readable media to implement functionality described above. Certain embodiments may be implemented using an existing computer processor, or by a special purpose computer processor incorporated for this or another purpose or by a hardwired and/or firmware system, for example. Certain embodiments include computer-readable media for carrying or having computer-executable instructions or data structures stored thereon. Such computer-readable media may be any available media that may be accessed by a general purpose or special purpose computer or other machine with a processor. By way of example, such computer-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of computer-executable instructions or data structures and which can be accessed by a general purpose or special purpose computer or other machine with a processor. Combinations of the above are also included within the scope of computer-readable media. Computer-executable instructions comprise, for example, instructions and data which cause a general purpose computer, special purpose computer, or special purpose processing machines to perform a certain function or group of functions.

Generally, computer-executable instructions include routines, programs, objects, components, data structures, etc., that perform particular tasks or implement particular abstract data types. Computer-executable instructions, associated data structures, and program modules represent examples of program code for executing steps of certain methods and systems disclosed herein. The particular sequence of such executable instructions or associated data structures represent examples of corresponding acts for implementing the functions described in such steps.

Embodiments of the present disclosure may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet, and may use a wide variety of different communication protocols. Those skilled in the art will appreciate that such network-computing environments will typically encompass many types of computer system configurations, including personal computers, handheld devices, multi-processor systems, microprocessor-based or programmable consumer electronics, network PCs, minicomputers, mainframe computers, and the like. Embodiments of the disclosure may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

Monitoring changes of the complex impedance of the circuit and applying chemometric analysis of the impedance spectra allows for the composition and continuous phase of oil-in-water and water-in-oil mixtures to be predicted with a standard error of 0.04% in 0-30% water and 0.26% in 30-100% water.

Multivariate analysis tools in combination with data-rich impedance spectra allow for elimination of interferences, and transducers designed for maximum penetration depth decreases the impact of fouling. As the penetration depth of the resonator is extended further into the bulk of the fluid, surface fouling becomes less significant.

The term "analyte" includes any desired measured environmental parameter.

The term "environmental parameters" is used to refer to measurable environmental variables within or surrounding a manufacturing or monitoring system. The measurable environmental variables comprise at least one of physical, chemical and biological properties and include, but are not limited to, measurement of temperature, pressure, material concentration, conductivity, dielectric property, number of dielectric, metallic, chemical, or biological particles in the proximity or in contact with the sensor, dose of ionizing radiation, and light intensity.

The term "fluids" includes gases, vapors, liquids, and solids.

The term "interference" includes any undesired environmental parameter that undesirably affects the accuracy and precision of measurements with the sensor. The term "interferent" refers to a fluid or an environmental parameter (that includes, but is not limited to temperature, pressure, light, etc.) that potentially may produce an interference response by the sensor.

The term "transducer" means a device that converts one form of energy to another.

The term "sensor" means a device that measures a physical quantity and converts it into a signal which can be read by an observer or by an instrument.

The term "multivariate data analysis" means a mathematical procedure that is used to analyze more than one variable from a sensor response and to provide the information about the type of at least one environmental parameter from the measured sensor spectral parameters and/or to quantitative information about the level of at least one environmental parameter from the measured sensor spectral parameters.

The term "resonance impedance" or "impedance" refers to measured sensor frequency response around the resonance of the sensor from which the sensor "spectral parameters" are extracted.

The term "spectral parameters" is used to refer to measurable variables of the sensor response. The sensor response is the impedance spectrum of the resonance sensor circuit of the resonant transducer 12. In addition to measuring the impedance spectrum in the form of Z-parameters, S-parameters, and other parameters, the impedance spectrum (both real and imaginary parts) may be analyzed simultaneously using various parameters for analysis, such as, the frequency of the maximum of the real part of the impedance (Fp), the magnitude of the real part of the impedance (Zp), the resonant frequency of the imaginary part of the impedance (F 1), and the anti-resonant frequency of the imaginary part of the impedance (F 2), signal magnitude (Z 1) at the resonant frequency of the imaginary part of the impedance (F 1), signal magnitude (Z 2) at the anti-resonant frequency of the imaginary part of the impedance (F 2), and zero-reactance frequency (Fz), frequency at which the imaginary portion of impedance is zero). Other spectral parameters may be simultaneously measured using the entire impedance spectra, for example, quality factor of resonance, phase angle, and magnitude of impedance. Collectively, "spectral parameters" calculated from the impedance spectra, are called here "features" or "descriptors". The appropriate selection of features is performed from all potential features that can be calculated from spectra. Multivariable spectral parameters are described in U.S. patent application Ser. No. 12/118,950 entitled "Methods and systems for calibration of RFID sensors", which is incorporated herein by reference.

The terminology used herein is for the purpose of describing particular embodiments only and is not intended to be limiting of the invention. Where the definition of terms departs from the commonly used meaning of the term, applicant intends to utilize the definitions provided herein, unless specifically indicated. The singular forms "a", "an" and "the" are intended to include the plural forms as well, unless the context clearly indicates otherwise. It will be understood that, although the terms first, second, etc. may be used to describe various elements, these elements should not be limited by these terms. These terms are only used to distinguish one element from another. The term "and/or" includes any, and all, combinations of one or more of the associated listed items. The phrases "coupled to" and "coupled with" contemplates direct or indirect coupling.

In some embodiments, the present invention uses the electric field and a single resonant coil that is capable of quantifying a large dynamic range, for example of 0-100% water, and characterizing the continuous phase of oil/water emulsions observed. Multiple sensing coils are not required to cover the broad dynamic range exhibited by fluids that are either oil/gas or water continuous phase. Without intending to be limited by theory, the ability to operate with a single sensing coil results from not using an eddy current based method wherein the power loss or attenuation of a magnetic field is determined and correlated to the conductive component content of a multiphase fluid.

Similarly, in at least some embodiments, the present invention does not require a combination of an eddy current or other transducer with a low frequency capacitance probe (or separate sensors to probe capacitance and conductance generally) in order to differentiate the complexity of the samples. In at least some embodiments of the presentinvention, only a single sensing coil and a second coil that both transmits and receives the signal are required.

In at least some embodiments of the present invention, sensing measurements are performed over a broad range of frequencies, where the range of frequencies includes regions where the resonator signal may be only 10%, 1% or even 0.001% from its maximum response. Sensing methods may include one or more of (1) to scan the sensor response over the where the range of frequencies includes regions where the resonator signal is only 0.001-10% from its maximum response, (2) to analyze the collected spectrum for the simultaneous changes to one or more of a number of measured parameters that included the resonance peak position, magnitude of the real part of the impedance, resonant frequency of the imaginary part of the impedance, antiresonant frequency of the imaginary part of the impedance, and others, (3) to determine the composition of fluid mixtures even when one of the fluids is at a low concentration, and (4) to determine fluid level and to determine emulsion layer. Spectrum information that is both slightly lower and higher in resonant frequency may be used. Optionally, a single coil may accomplish two functions—excitation and receiving signal, optionally simultaneously.

At least some embodiments of the present invention employ two coils with resonant frequencies with baseline separation between the frequency bands. In this way, the intrinsic resonant signal of the pick-up coil (which may be used as both the transmission and receiving coil) does not influence the resonance signal of the sensing coil.

U.S. application Ser. No. 13/630,587 and U.S. application Ser. No. 13/630,739, both filed on Sep. 28, 2012 by General Electric Company, are incorporated herein.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements.

We claim:

1. A sensor comprising:
a resonant transducer, wherein the resonant transducer comprises:
a sampling cell;
a bottom winding disposed around the sampling cell; and
a top winding disposed around the bottom winding and the sampling cell, wherein the bottom winding is floating and the bottom winding is excited by an electro-magnetic field created by a power wave flowing through the top winding such that the bottom winding generates a second electro-magnetic field that is altered by its interaction with an emulsion or other dispersion in the sampling cell and the second electro-magnetic field is sensed by the top winding.

2. The sensor of claim 1 wherein the top winding is at least half as long as the bottom winding.

3. The sensor of claim 1 wherein the sampling cell is an open tube.

4. The sensor of claim 1 wherein the top winding has a greater pitch than the bottom winding.

5. The sensor of claim 1 comprising a galvanic isolator between the top winding and the bottom winding.

6. The sensor of claim 1 wherein the top winding is connected to a data collection system and to a power supply.

7. A sensor comprising,
a sampling cell adapted to hold a stationary or flowing liquid;
a bottom winding disposed around the sampling cell; and
a top winding disposed around the bottom winding and the sampling cell, wherein the bottom winding is floating and the bottom winding is excited by an electro-magnetic field created by a power wave flowing through the top winding such that the bottom winding generates a second electro-magnetic field that is altered by its interaction with the liquid or other dispersion in the sampling cell and the second electro-magnetic field is sensed by the top winding.

8. The sensor of claim 7 wherein the top winding is at least half as long as the bottom winding.

9. The sensor of claim 7 wherein the sampling cell is a tube.

10. The sensor of claim 9 wherein the tube is made of a galvanic isolating material.

11. The sensor of claim 7 wherein the top winding has a greater pitch than the bottom winding.

12. The sensor of claim 7 wherein the top winding has one tenth or few coils than the bottom winding.

13. The sensor of claim 7 wherein the top winding is connected to a power supply, a signal analyzer or both.

14. The sensor of claim 7 wherein the top winding and the bottom winding have baseline separation.

15. The sensor of claim 7 comprising a galvanic isolator between the top winding and the bottom winding.

16. The sensor of claim 7 comprising a spacer around the top winding.

17. The sensor of claim 16 comprising a radio frequency absorber around the spacer.

18. The sensor of claim 17 comprising a metal shield around the radio frequency absorber and a cover around the metal shield.

19. The sensor of claim 13, wherein a fluid phase inversion point is determined by the signal analyzer from values of a complex impedance spectrum of the liquid measured by the top winding by identifying a change in the impedance values.

20. The sensor of claim 19, wherein the signal analyzer assigns a value for an interface level based on the fluid phase inversion point.

* * * * *